(12) United States Patent
Bailey et al.

(10) Patent No.: US 10,806,415 B2
(45) Date of Patent: Oct. 20, 2020

(54) CT IMAGING SYSTEMS

(71) Applicant: Dedicated2Imaging, LLC, Portsmouth, NH (US)

(72) Inventors: Eric M. Bailey, North Hampton, NH (US); Andrew Tybinkowski, Silver Lake, NH (US)

(73) Assignee: Dedicated2Imaging, LLC, Portsmouth, NH (US)

( * ) Notice: Subject to any disclaimer, the term of this patent is extended or adjusted under 35 U.S.C. 154(b) by 36 days.

(21) Appl. No.: 16/073,869

(22) PCT Filed: Apr. 11, 2017

(86) PCT No.: PCT/US2017/026917
§ 371 (c)(1),
(2) Date: Jul. 30, 2018

(87) PCT Pub. No.: WO2017/180566
PCT Pub. Date: Oct. 19, 2017

(65) Prior Publication Data
US 2019/0357862 A1    Nov. 28, 2019

Related U.S. Application Data

(60) Provisional application No. 62/320,622, filed on Apr. 11, 2016.

(51) Int. Cl.
| | |
|---|---|
| *A61B 6/03* | (2006.01) |
| *A61B 6/00* | (2006.01) |
| *A61B 6/04* | (2006.01) |
| *A61G 3/00* | (2006.01) |

(52) U.S. Cl.
CPC ............ *A61B 6/4405* (2013.01); *A61B 6/035* (2013.01); *A61B 6/04* (2013.01); *A61B 6/0457* (2013.01); *A61B 6/4411* (2013.01); *A61B 6/4476* (2013.01); *A61B 6/548* (2013.01); *A61G 3/001* (2013.01)

(58) Field of Classification Search
CPC .................................... A61B 6/03; A61B 6/44
See application file for complete search history.

(56) References Cited

U.S. PATENT DOCUMENTS

| | | | | |
|---|---|---|---|---|
| 5,515,416 A * | 5/1996 | Siczek | ................ | A61B 6/4014 378/196 |
| 5,901,200 A * | 5/1999 | Krause | ................ | A61B 6/4405 378/197 |
| 6,431,751 B1 * | 8/2002 | Everett | ................ | A61B 6/4233 378/193 |

(Continued)

FOREIGN PATENT DOCUMENTS

| | | |
|---|---|---|
| DE | 202013007567 U1 | 10/2013 |
| JP | 2003310605 A | 11/2003 |

*Primary Examiner* — Thomas R Artman

(57) ABSTRACT

New and improved CT imaging systems are presented which improve the ability to deploy CT imaging in a mobile setting, such as in an ambulatory setting or as part of a mobile hospital unit. Improvements disclosed include implementation of an internal drive system for moving a scanner component relative to a fixed or static platform/base, improved modularity of components for quick maintenance/ repair and the inclusion of an integrated patient alignment mechanism connected directly to the CT system.

8 Claims, 16 Drawing Sheets

(56) References Cited

U.S. PATENT DOCUMENTS

| | | | |
|---|---|---|---|
| 7,001,045 B2* | 2/2006 | Gregerson | A61B 6/035 362/253 |
| 7,607,832 B2* | 10/2009 | Jensen | A61B 6/4405 378/197 |
| 7,658,540 B2* | 2/2010 | Jensen | A61B 6/4405 378/197 |
| 7,905,659 B2* | 3/2011 | Gregerson | A61B 6/035 378/197 |
| 8,118,488 B2* | 2/2012 | Gregerson | A61B 5/0555 378/198 |
| 8,308,361 B2* | 11/2012 | Gregerson | A61B 6/035 378/197 |
| 8,905,637 B2* | 12/2014 | Tybinkowski | A61B 6/04 378/209 |
| 9,408,554 B2* | 8/2016 | Gregerson | A61B 5/0555 |
| 9,700,272 B2* | 7/2017 | Gregerson | A61B 5/0555 |
| 9,820,706 B2* | 11/2017 | Fortuna | A61B 6/4435 |
| 10,136,867 B2* | 11/2018 | Fortuna | A61B 6/4435 |
| 2003/0235266 A1* | 12/2003 | Gregerson | A61B 6/035 378/4 |
| 2008/0212743 A1* | 9/2008 | Gregerson | A61B 6/035 378/197 |
| 2010/0172468 A1* | 7/2010 | Gregerson | A61B 5/0555 378/20 |
| 2010/0205740 A1* | 8/2010 | Tybinkowski | A61B 6/04 5/601 |
| 2011/0200175 A1* | 8/2011 | Gregerson | A61B 6/035 378/197 |
| 2012/0136196 A1 | 5/2012 | Foxall et al. | |
| 2012/0330087 A1* | 12/2012 | Gregerson | A61B 5/0555 600/7 |
| 2015/0282774 A1 | 10/2015 | Lee et al. | |
| 2016/0015343 A1* | 1/2016 | Fortuna | A61B 6/4435 378/51 |
| 2016/0015344 A1* | 1/2016 | Fortuna | A61B 6/4435 378/51 |
| 2016/0242705 A1 | 8/2016 | Richardson | |
| 2016/0338656 A1* | 11/2016 | Gregerson | A61B 5/0555 |
| 2018/0070900 A1* | 3/2018 | Fortuna | A61B 6/4435 |
| 2018/0125440 A1* | 5/2018 | Gregerson | A61B 5/0555 |
| 2019/0105004 A1* | 4/2019 | Fortuna | A61B 6/4435 |
| 2019/0357862 A1* | 11/2019 | Bailey | A61B 6/4411 |

* cited by examiner

A

B

CT IMAGING SYSTEMS

CROSS-REFERENCE TO RELATED SECTIONS

The subject application claims the benefit of U.S. Provisional Application Ser. No. 62/320,622 filed Apr. 11, 2016 and entitled "CT Systems with Internal Drive System, Modularity and Alignment Head Board" the contents of which are hereby incorporated herein in their entirety.

BACKGROUND

The subject application relates to computerized tomography (CT) imaging. In particular, new and improved CT imaging systems are presented which improve the ability to deploy CT imaging in a mobile setting, such as in an ambulatory setting or as part of a mobile hospital unit. Example improvements disclosed herein include implementation of an internal (i.e., self-contained) drive system for moving a scanner component relative to a fixed or static platform/base, improved modularity of components for quick maintenance/repair and the inclusion of an integrated patient alignment mechanism such as an alignment head board directly connected to the CT system to improve system reliability. The improved CT systems presented herein have many uses across a number of different settings including both ambulatory settings and hospital settings.

Mobile Ambulatory Settings:

Stroke and Traumatic Brain Injury (TBI) are the number 3 and 4 leading causes of death in the developed world, and are the number 1 and 2 causes of long term disability. The total USA societal cost of these medical issues exceeds $100 B annually. Close to 1 Million people experience a Stroke each year in the USA alone. There is only one effective acute therapy for the major sub-type of stroke known as Ischemic Stroke. Approximately 80% of all strokes are ischemic strokes, which could benefit from clot-dissolving IV thrombolytic therapy followed closely by interventional neuro-radiologic intervention. Sadly, less than 3% of ischemic stroke patients in the USA receive this therapy. The major reason for this low treatment rate is the lengthy time in performing the diagnostic stroke workup, which consists primarily in performing a non-contrast CT to rule out hemorrhagic stroke. Unfortunately, thrombolytic therapy is neither safe nor effective if administered longer than 3 hours from symptoms.

Recently, Mobile Stroke Units have been developed and deployed in both in Europe and the USA, which contain CT systems and tele-stroke communication equipment in an ambulatory settings, e.g., mobile ambulatory settings. Advantageously, these Mobile Stroke Units are able to greatly reduce medical intervention response times by providing earlier access to CT data. The reduced response time in turn lends to greater accessibility to and effectiveness of treatment options such as thrombolytic therapy. Thus, there exists a need for new and improved CT systems which may be deployed in an ambulance, first response vehicle, or other mobile ambulatory setting. In particular, existing ambulatory CT solutions are largely based on older/larger hospital designs and are therefore often difficult to mount, transport, use and maintain, particularly in a mobile ambulatory setting. The improved CT solutions presented herein address many of these deficiencies.

Hospital Settings:

Many stroke and TBI patients experience lengthy intensive care unit (ICU) stays. Mixed with a variety of other patients such as heart attack, this cohort of ICU patients requires frequent CT scans as part of the standard of care. Unfortunately, the back and forth transportation of patients to a fixed CT scanner has been proven to be costly and dangerous. Moreover, such transportation of patients requires ICU personnel to leave the floor of the ICU thereby depleting and taxing ICU coverage. Today there are over 500 installations of ICU Generation 1 CT scanners. This generation one design is over 10 years old and many hospitals are long due for an upgrade. Thus, there exists a need for new and improved hospital CT systems and, in particular, a need for new and improved mobile CT systems, e.g., which can be used without the need to transport patients to another area of the hospital (e.g., which can be used in the ICU, Emergency Department (ED), or other hospital floor type setting or in an operating room type setting. Existing mobile CT solutions often times employ an external type drive system which translates the CT system relative to the floor. Such systems are often times hampered by reliability problems arising from uneven floors and stability issues. Moreover similar to the mobile ambulatory setting, existing mobile CT solutions, often times present transportation, usability and maintenance challenges. For example, alignment/integration of existing mobile CT systems with the various differing types of patient beds/stretchers is often difficult and subject to human error and patient misalignment may often result in signal degradation and the proliferation of image artifacts. Again, the improved CT solutions presented herein address many of these deficiencies.

SUMMARY

New and improved CT imaging systems are presented which improve the ability to deploy CT imaging in a mobile setting, such as in an ambulatory setting or as part of a mobile hospital unit. Improvements disclosed include implementation of an internal drive system for moving a scanner component relative to a fixed or static platform/base, improved modularity of components for quick maintenance/repair and the inclusion of an integrated patient alignment mechanism connected directly to the CT system.

Example embodiments include a CT system comprising a scanner component, a base component mounted relative to a floor of a vehicle, and an internal drive component for translating the scanner component relative to the base component. Advantageously, the base component may include a low profile base component configured to minimize the space between the scanner component and the floor of the vehicle. For example, a distance between the bottom of the scanner component and the floor may be less than 2 feet, less than 1 foot or most preferably less than 6 inches. In some embodiments, the base component is a low profile base component configured to align an opening of the scanner component at substantially the same height as a patient secured in the vehicle on a collapsed stretcher. Thus, e.g., a distance between the center of the opening and the floor may be less than 3 feet or more preferably less than 2 feet. In example embodiments, the CT system may further include a patient alignment mechanism, e.g., a headboard, mounted directly to the CT system, e.g., mounted relative to the base component. Advantageously, the CT system may include a plurality of modular subsystems such as an x-ray source sub-system, a detection sub-system, a control sub-system and/or a power sub-system.

In further example embodiments, a CT system is provided comprising a scanner component, a base component mounted relative to a mobile cart, and an internal drive component for translating the scanner component relative to the base component. This CT system may likewise include a patient alignment mechanism, e.g., a headboard, mounted directly to the CT system, e.g., mounted relative to the base component. Furthermore this CT system may also include a plurality of modular subsystems such as an x-ray source sub-system, a detection sub-system, a control sub-system and/or a power sub-systems. Advantageously, the mobile cart may include an omni-directional drive system for transporting the mobile cart.

In further example embodiments, a CT system is provided comprising a scanner component, a base component, and an internal drive component for translating the scanner component relative to the base component, wherein the base component is configured for interchangeably mounting relative to either a vehicle floor or a mobile cart.

In further example embodiments, a scanner component of a CT system is provided, the scanner component comprising a radiation source and detection components mounted to a rotatable disk, wherein the rotatable disk is rotatably mounted relative to a housing of the scanner component via a gantry, wherein the gantry is translatably mounted relative to the housing so as to enable translation of the gantry and rotatable disk relative to the housing whereby a beam path of the scanner component is translated relative to the housing. Advantageously, one or more threaded rods may be used for mounting the gantry relative to the housing, wherein rotationally driving the one or more threaded rods translates the gantry relative to the housing.

In further example embodiments, a CT system is provided comprising a scanner component, a base component, and an internal drive component for translating the scanner component relative to the base component, wherein the scanner component is further pivotable relative to the base component so as to allow for a lowering of a center of gravity thereof.

In further example embodiments, a CT system is provided comprising a scanner component, a base component, an internal drive component for translating the scanner component relative to the base component, and an alignment mechanism mounted relative to the base component for aligning with a patient platform.

In further example embodiments, a CT system is provided comprising a scanner component, a base component, an internal drive component for translating the scanner component relative to the base component, and a user interface assembly tethered relative to the CT system and including a wired connection for enabling remotely controlling the CT system from a radiation shielded location.

In further example embodiments, a CT system is provided comprising a scanner component, a base component, and an internal drive component for translating the scanner component relative to the base component, wherein the scanner includes first and second nested housings.

BRIEF DESCRIPTION OF THE DRAWINGS

The present disclosure is further described in the detailed description which follows, in reference to the noted plurality of drawings by way of non-limiting examples of embodiments of the present disclosure.

DETAILED DESCRIPTION

Figure 1:
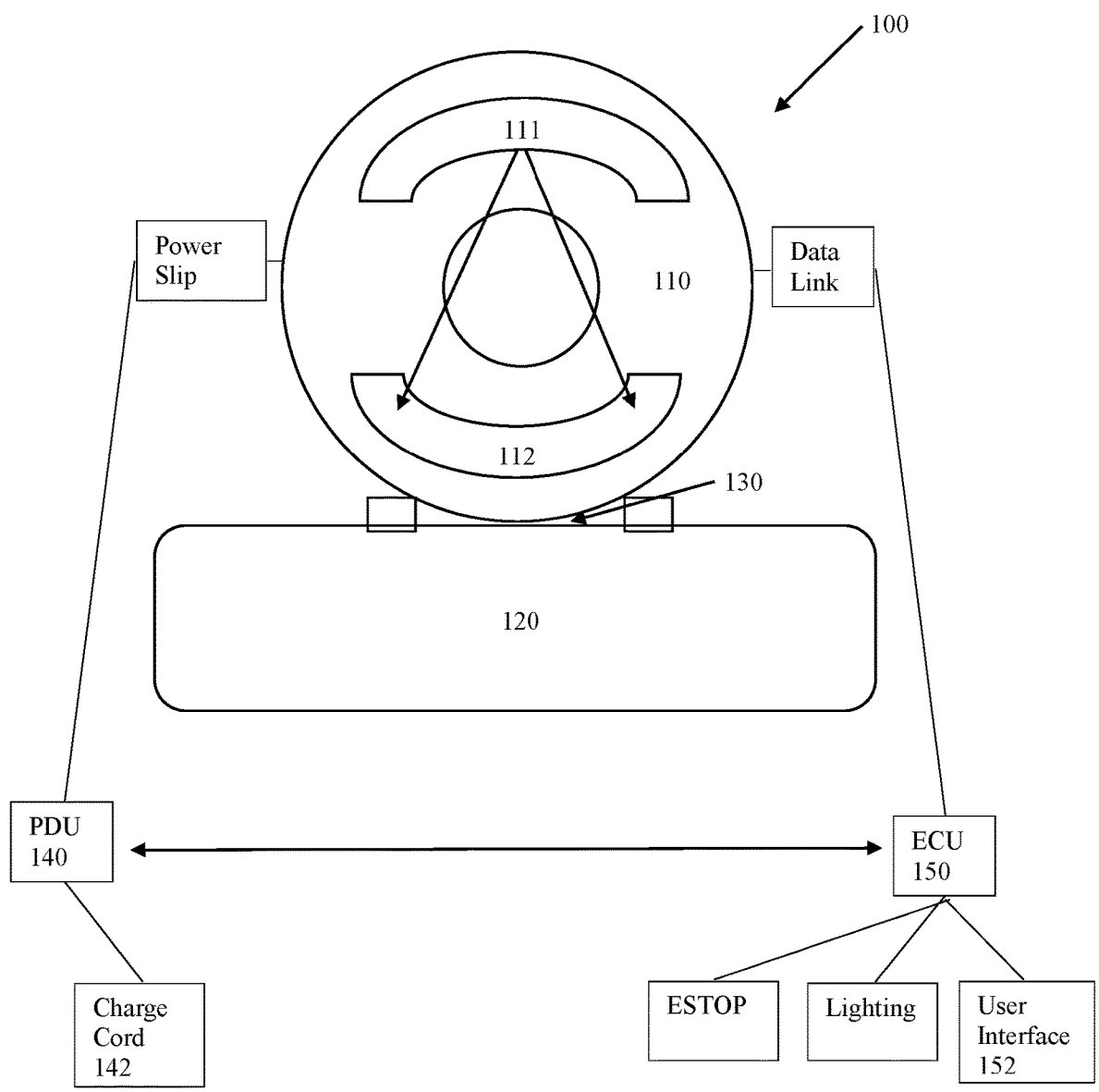
FIG. 1 depicts an exemplary system block diagram of a CT system, according to embodiments of the present disclosure.

New and improved CT imaging systems are presented herein, which improve the ability to deploy CT imaging in a mobile setting, such as in an ambulatory setting or as part of a mobile hospital unit.

In example embodiments, the new and improved CT imaging systems may include an internal (i.e. self-contained) drive system for moving a scanner component of the system relative to a fixed or static platform/base component of the system during scanning. Advantageously, the use of an internal drive system (as opposed to an external drive system wherein the entire CT imaging system is moved relative to the floor during scanning) improves the stability of the system and reliability of the scan. Multiple different types of platforms/bases may then be employed depending on the specific application. For example, in some embodiments, the platform/base may be low platform/base, e.g., adapted for mounting, to a floor of an ambulance or other first response vehicle. Advantageously, the low platform/base may be adopted to minimize/reduce a distance between a scanner component of the system and the ground/floor where the system is mounted, thereby lowering the center of gravity of the system. In example embodiments, the distance between a bottom of the scanner component and floor may be less than 2 feet, less than 1 foot, or even less than six inches. In further example embodiments, the scanner component may be adapted/configured to pivot or otherwise fold down so as to further reduce the center of gravity of the system, e.g., during transport. In yet further example embodiments, the scanner component may be adapted/configured to translate and/or pivot from a scanning position to a storage position during transport, such as adjacent a front or side wall of an ambulatory or first response vehicle.

Notably, in example embodiments, the scanner component may be generally cylindrically shaped with a center opening configured. e.g., sized/shaped, for receiving a portion of a patient's anatomy (such as the patient's head). In use, the scanner component may house an x-ray source sub-system and a detection sub-system which are generally rotated about the portion of the patient's anatomy, e.g. in a continuous manner, as the scanner component is moved laterally thereby producing a CT scan for the patient. In example embodiments, the low platform/base may be adopted to minimize/reduce a distance between the scanner component opening and the ground/floor where the system is mounted, thereby lowering the center of gravity of the patient during scanning. In example embodiments, the distance between the center of the opening of the scanner component and floor may be less than 3 feet or even less than 2 feet.

The lowering of the center of gravity of the system and or of the patient during scanning may be particularly advantageous with respect to transportation in an ambulance or other first response vehicle, where weight distribution, handling and safety concerns require that the vehicle and patient maintain a low center of gravity.

In other example embodiments, the platform/base component of the system may be a mobile platform/base, e.g., a same or similar to mobile platform/base as currently available for mobile non-CT x-ray type systems. Advantageously, the mobile platform/base may include a motorized mobility assist or type of drive system for facilitating transportation of the CT system throughout the hospital. In example embodiments, the mobile platform/base may be utilized to house control sub-system components and/or power sub-system components. Alternatively, the control sub-system components and/or power sub-system components may be external to the CT system. In some embodiments, the mobile platform/base may include a multi-directional drive system configured for independently controlling movement in multiple horizontal dimensions, e.g., forward/back and side-to-side. In some embodiments, the multi-directional drive system may be an omni-directional drive system such as a holonomic drive system which includes 3 degrees of freedom and is therefore able to shift from side-to side or strafe diagonally without changing the direction of its wheels. In some embodiments, omni-wheels or mecanum wheels or the like may be utilized to implement the omni-directional drive system. The use of omni-wheels or mecunum wheels may advantageously minimize surface drag and torque. Advantageously an H-drive drivetrain system may be utilized to supply power to each wheel station.

In some embodiments, radiation shielding panels or curtains may be secured relative to and, in some embodiments, may pivot, extend or otherwise deploy from the platform/base component. In this way, the radiation shielding may be deployed and remain stationary relative to a patient during scanning process.

Advantageously, in some embodiments, the new and improved CT imaging systems presented herein include modular type designs which facilitate maintenance/adaptability thereof. For example, as noted above, a same scanner component and internal drive system may be utilized in conjunction with different bases/platforms depending on the particular application, Thus, in some embodiments, the CT scanning component and internal drive system may be configured to enable mounting thereof relative to a plurality of different types of bases/platforms. In this way a hospital may easily refit a single machine for different purposes. Similarly, in some embodiments, the bases/platforms presented herein may be adapted to enable mounting different types of imaging modalities, such CT, x-ray, ultrasound etc. This adaptable/interchangeable modular type design also increases manufacturing efficiencies in producing the individual components.

Notably, the modular design approach disclosed herein extends with respect to functional sub-systems of the CT systems presented herein. For example, the x-ray source sub-system and detection sub-system may be modular components of the scanner component. Similarly, the control sub-system and/or power sub-system may be modular components of the base/platform component. Thus, in example embodiments, repair of a damaged sub-system may be facilitated by simply swapping out the entire modular sub-system for a new working sub-system. In this way the CT system may continue to function while the replaced damaged sub-system is repaired. Thus, in example embodiments a modular design may include 1) a modular x-ray source sub-system, e.g., including an x-ray source, collimator, transmission lenses/optics, filters, etc., 2) a modular detection sub-system, e.g., including a detection array, receiving lenses/optics, filters such as scatter filters, etc. 3) a modular control sub-system, e.g., including scanner position controls, data processing components, network integration components, etc. and 4) a modular power sub-system, e.g., including a battery, converters, power regulators, surge protectors, etc.) While exemplary embodiments envision a four subsystem modular component design it should be appreciated that other modular configurations may be employed. For example, in some embodiments, the control sub-system may include several distinct interchangeable modular components.

In further exemplary embodiments, the CT imaging systems described herein may advantageously include a user interface control assembly including, e.g., a touch screen tablet type control assembly. Advantageously the user interface control assembly may include a wired or tethered connection relative the CT imaging system, e.g., relative to a base of the system and/or relative to a scanner component of the system. In some embodiments, the user interface control assembly may be removably dockable with the CT imaging system and the tethered or wired connection may be retractable so as to facilitate storage/coiling of the wire or tether when the user interface assembly is docked with the CT imaging system. The wire or tether may advantageously allow for wired operation of the CT imaging system from a remote location, e.g., radiation shielded location. In example embodiments, safety features may mandate scanner operation only where the user interface control assembly is in a non-docked position. In some embodiments, the wire or tether may be reinforced and act as a security cable for preventing theft or loss of the user interface control assembly. The user interface control assembly may further be configured to interface wirelessly with one or more remote work stations and/or mobile devices.

As noted above, proper alignment of the patient (e.g., of the portion of the patient's anatomy being scanned), is important achieving a proper scan and reducing image noise/artifacts. Thus, in further example embodiments, the new and improved CT imaging systems presented herein may include an integrated patient alignment mechanism (such as an alignment head board directly) which is directly connected to the CT system. In particular the alignment mechanism may be secured relative to the base/platform of the system. This can be contrasted with existing CT systems where alignment is typically achieved via patient platforms, such as patient beds, stretchers, tables, etc., (in may existing CT systems, special adaptors are required to interface a given patient platform with the system). The use of an integrated patient alignment mechanism that is secured relative to the CT system as opposed to the patient platform ensures greater reliability and improves the ease of use of the CT system by negating the need for different adapters depending for different types of patient platforms. In some embodiments, the integrated alignment mechanism may advantageously include a latch or other releasable locking mechanism for securing the alignment mechanism relative to a patient platform. In some embodiments, a secure connection between the alignment mechanism and the patient platform may be required prior to initiating any scan. In further example embodiments, the integrated alignment mechanism may advantageously include one or more patient alignment features for guiding positioning of a patient, e.g., of a particular portion of a patient's anatomy, relative to the alignment mechanism. For example, the patient guide features may include markings, projections, grooves or other patient alignment features for positioning and orientating a patient relative to the alignment mechanism. The integrated alignment mechanism may further include one or more patient fasteners for securing a patient, e.g., a particular portion of a patient's anatomy in a particular position/orientation relative to the alignment mechanism. Thus, for example, in some embodiments, the integrated alignment mechanism may include one or more straps, ties, belts, clips or other patient fasteners.

Advantageously, the integrated patient alignment mechanism may be configured for a particular portion of the patient's anatomy. For example, in some embodiments, the patient alignment mechanism may include a headboard secured relative the system and adapted to facilitate proper alignment of a patient's head. In some embodiments, the patient alignment mechanism may be interchangeable, e.g., in order to enable selection of the appropriate alignment mechanism for a particular portion of the patient's anatomy. In further example embodiments, the patient alignment mechanism may define a plurality of different alignment configurations for the same portion of the patient's anatomy. These different alignment configuration may, e.g., correspond to different scanning protocols/applications. In some embodiments, the patient alignment mechanism may enable controllably adjusting a position and/or orientation of a portion of the patient's anatomy, e.g., to a selected position/orientation. Notably, the CT system may be configured to register the selected configuration of the patient alignment mechanism with respect to the corresponding image data. In further example, embodiments, scanning protocols/applications may be pre-registered for a particular alignment mechanism and/or configuration thereof. Thus, in some embodiments, confirmation of a particular alignment mechanism and/or configuration thereof may be required by the system prior to initiating a corresponding scanning protocol/application. In some embodiments, a scan sequence may be facilitated by automatically adjusting or otherwise guiding adjustment of patient orientation/alignment between scans. For example, in some embodiments, a scan sequence may involve automatically adjusting or otherwise prompting adjustment of a configuration of the alignment mechanism between scans. In other embodiments, a scan sequence may involve prompting swapping of a first alignment mechanism for a second alignment mechanism between scans.

In example embodiments, the CT systems presented herein may include a mechanism for selectively/adjustably orienting the CT scanner component and/or internal drive system relative to a mounting surface. This may facilitate mounting the system on in inclined surface or may facilitate adjusting the orientation of the scanner component to match an orientation of a portion of the patient's anatomy. For example in some embodiments, it may be desirable to orient the CT scanner component and internal drive system at an angle relative to a giving mounting surface. In further example embodiments, it may be desirable to allow for selectively changing the scanner orientation from a horizontal scanner to a vertical scanner. In further example embodiments the CT systems presented herein may include mechanisms for selectively/adjustably positioning (e.g., translating) the CT scanner component and/or internal drive system relative to a mounting surface. For example, in some embodiments, a vertical and/or horizontal position of the scanner component may be adjustable, e.g., so as to allow for alignment with a patient and/or patient platform, e.g., height alignment. In example embodiments, an integrated patient alignment mechanism (such as described herein) may be utilized to guide such orientating and/or positional alignment of the scanner component and/or internal drive system. Thus, for example, a scanner component may be translated vertically relative to a mounting surface such that an integrated alignment mechanism is vertically aligned with a patient platform. In some embodiments, alignment with a patient and/or patient platform may be automatic, e.g., based on preprogramed positions for different types of patient platforms and/or different scanning procedures and/or based feedback from one or more sensors, e.g., optical sensors, pressure sensors, etc. In further example embodiments, a position of the scanning component relative to a base may be automatically or manually adjusted based on a selected alignment mechanism. Thus, in example embodiments and alignment mechanism is selected and attached relative to a base of the CT system. A position of the scanning component (relative to the base) may then be automatically or manually adjusted so that the opening of the scanning component is correctly aligned with the selected alignment mechanism.

In some embodiments, active safety features may be included which limit or otherwise safeguard against motion of the CT system (e.g., transport, alignment, and/or scanning type motion) that could potentially harm a patient or cause damage to the system. For example, in some embodiments, sensors such as optical, pressure or resistance based sensors may be utilized to detect proximity of one or more components of the CT system relative to a patient or object and provide passive feedback (e.g., an alarm or alert) or active feedback (automatic breaking or other motion limitations) based on such proximity detection. In some embodiments, passive and/or active feedback may be subject to manual override.

In further example embodiments, the CT systems presented herein may include an internal translational mechanism for the CT scanning component. Thus, e.g., rather than the CT scanning component translate relative to a base, in some embodiments, an internal disk or drum of the scanning component may translate relative to a stationary housing. As noted above, the housing may generally be cylindrically shaped with a center opening. In general a rotating disk or drum assembly may be included within the housing for mounting CT components such as radiation source and detector components on opposite sides of the center opening. The rotating disk or drum assembly is typically rotationally mounted relative to the housing via a rotational gantry, e.g., including one or more bearing runs. In particular, the gantry may include an annular outer support having a radially inwardly facing, continuous circumferential bearing chamber including two circumferential bearing runs within the bearing chamber where roller bearings in the bearing runs rotatable support a circumferential lip of the drum or disk within the outer support, such that the drum or disk is rotatable about an axis of rotation. A belt or gear drive system may be utilized to drive rotation of the drum or disk within the housing. For example a poly-v belt drive system or other belt drive system may be utilized to transfer rotation from a drive pulley, e.g., a sheaved drive pulley, to the drum or disk. Notably, the rotational mounting and drive components of the systems described herein are not limited to particular examples provided above. Indeed other rotational gantries and rotational drive mechanisms may also be utilized. For example, in some embodiments, a magnetic bearing system, air bearing system of other rotational mounting may be utilized. In further embodiments, the CT imaging systems described herein may utilize a direct drive type system with a direct drive gantry motor. Advantageously, in embodiments described herein, the rotational gantry may be translatably mounted relative to the housing of the scanner component. Thus, e.g., in some embodiments, the gantry may be mounted relative the housing via one or more threaded rods, e.g., where rotation of the rod(s) results in translational movement of the gantry relative to the housing. The result of the embodiments described above is a scanning component with a variable beam path position. Thus, rather than translate the scanning component, the scanning component may remain stationary while the beam bath is shifted internally by translation of the of the rotation drum/disk.

In further example embodiments, the CT systems presented herein may include a nested, e.g., a telescopic scanner component configuration. In a nested configuration a first housing of the CT scanner component may be advantageously nested within a second housing of the CT scanner component. In some embodiments, the second housing may include an inner diameter substantially equal to the outer diameter of the first housing. Moreover, in some embodiments, the second housing may have a greater length than the first housing. Thus, in some embodiments a first ring-shaped housing member may be positioned within a second ring-shaped housing, e.g., proximal to a first open end thereof. In general, the first and second housings may be shaped as nested right circular hollow cylinders. Advantageously, the first housing may define an inner opening configured. e.g., sized/shaped, for receiving a portion of a patient's anatomy (such as the patient's head) while the second housing may define a wider opening configured for receiving a greater portion of a patient's anatomy (such as a patients head neck and shoulders). In some embodiments, the outer housing may advantageously act as a radiation shield, e.g., to help contain radiation from the scanner component and mitigate radiation scatter. In further embodiments, the first housing may be stationary or fixed relative to the second housing. Thus, in some embodiments, the first housing may include an internal translation drive for translating a rotatable disk/drum housed therein (e.g., thereby translating a beam bath relative to a patient). In other embodiments, the first housing may be configured to translate relative to the second housing. In some embodiments, this may be for storage/alignment purposes, e.g., for enabling collapsing the first housing into the second housing so as to reduce a size footprint of the CT scanner component when the scanner component isn't in use, so as to enable positioning of the scanner relative a portion of a patient's anatomy to be scanned and/or so as to enable positioning the first and our second housing in a position to provide optimal radiation shielding for a particular scan position. In some embodiments, the second housing may be configured to telescopically extend relative to the first housing, e.g., prior to initiating a scan. In further embodiments, the first housing may be configured to translate relative to the second housing so as to implement a scan (e.g., so as to translate a beam path relative to the patient). Thus, in some embodiments, the first and/or second housing may be positioned relative to the patient so as to align the CT scanner component with the patient. The first and/or second housings may also be positioned relative to each other to provide optimal radiation protection or to expand an inner cavity space for a scan. A scan may then be initiated by translating the first housing relative to the second housing (e.g., so as to translate a beam path relative to the patient). Notably, to provide optimal radiation shielding the CT scanner component may be configured such that the beam path is maintained in a central positioning relative to the first and/or second housing(s). This may advantageously minimize radiation scatter and unwanted exposure by the patient and/or a care provider.

In example embodiments, a highly modular CT system is presented, which can be configured into a portable ICU scanner when sitting on a portable x-ray base (such as on a Siemens portable x-ray base), or which may be reconfigured inside a mobile stroke vehicle where the CT is on the base of the vehicle floor and the major electronics are external/remote. The scan user interface may be greatly simplified for example, limited to present protocols (e.g., one or two preset protocols). A simple interface to scan and communicate and transfer data to a HIS/RIS/PACS system may be included (e.g., in Siemens Syngo format). Moreover the system may be manufacture utilizing pre-existing components such as DAS, Detector, X-ray tube, HVPS, workstation software, recon software, and portable base. In a mobile ambulatory stetting, the CT system may be directly integrated/packaged with a vehicle, a telemedicine system and/or other medical equipment.

With initial reference to FIG. 1, an exemplary system block diagram of a CT system 100 is depicted, according to embodiments of the present disclosure. The CT system includes a scanner component 110 in the form of a Ring/Doughnut assembly which comprises two major assemblies: A) the x-ray generation box 111 which has x-ray tube, high voltage power supply (HVPS), collimator, etc. and B) the data acquisition system (DAS)/Detector/Control box 112 which contains all the detectors, spine, DAS, LVPS (low voltage power supply), interface electronics, data link electronics, etc. An internal drive system 130 is also included for translating the scanner component 110 (e.g., in one or more axes) relative to a base/platform component 120.

Advantageously, in some embodiments, the internal drive system 130 may include one or more slides and/or tracks for defining a translational relationship between the scanner component 110 and the base/platform component 120 (e.g., a single slide centered relative to a bottom of scanner component or dual parallel slides on opposing sides of the bottom of the scanner component). Furthermore, the internal drive system 130 may include one or more drive mechanisms such as ball screws, actuators or the like, for driving the translational movement (e.g., a single ball screw centered relative to a bottom of scanner component or dual parallel ball screws on opposing sides of the bottom of the scanner component. In example embodiments, the internal drive system 130 may be specifically configured to mitigate/prevent rotational drifting during translation. Thus, in preferred embodiments, the internal drive system is operatively coupled relative to a bottom portion of the scanner component 110 (i.e. as opposed to side or top portions of the scanner component). Moreover, while dual drive mechanism(s) may be utilized (e.g., dual ball screws), it is preferable that the drive mechanisms be mechanically synched, for example, share a common drive motor/drive transmission, (such as mechanically synching the rotation of dual ball screws via a common drive belt). Note that in some embodiments, slide mechanism(s) may not be needed and the scanner component 110 may instead be directly supported by the drive mechanism(s).

The system 100 may further include a power distribution unit (PDU) assembly 140 (that contains the power electronics and batteries) and Electronic Control Unit (ECU) assembly 150 (that contains the control, recon, and interface electronics) which may be connected to the scanner component 110 via a power slip and a data link, respectively. The ECU assembly 150 may further be operatively connected relative to a user interface (UI), and other control subsystems such as an emergency stop (estop) and lighting modules. As noted above, the ECU assembly 150 may include a tethered/wired user interface control assembly for remote wired operation of the CT imaging system. Furthermore the PDU assembly may advantageously be configured to require a minimal external power supply connection prior to allowing for operation of the CT imaging system. Thus, e.g., while the CT imaging system may include a battery back-up system for supplementing an irregular power supply, e.g., from a wall connection, a wired power supply connection may be required prior to operation of the device.

Figure 2:
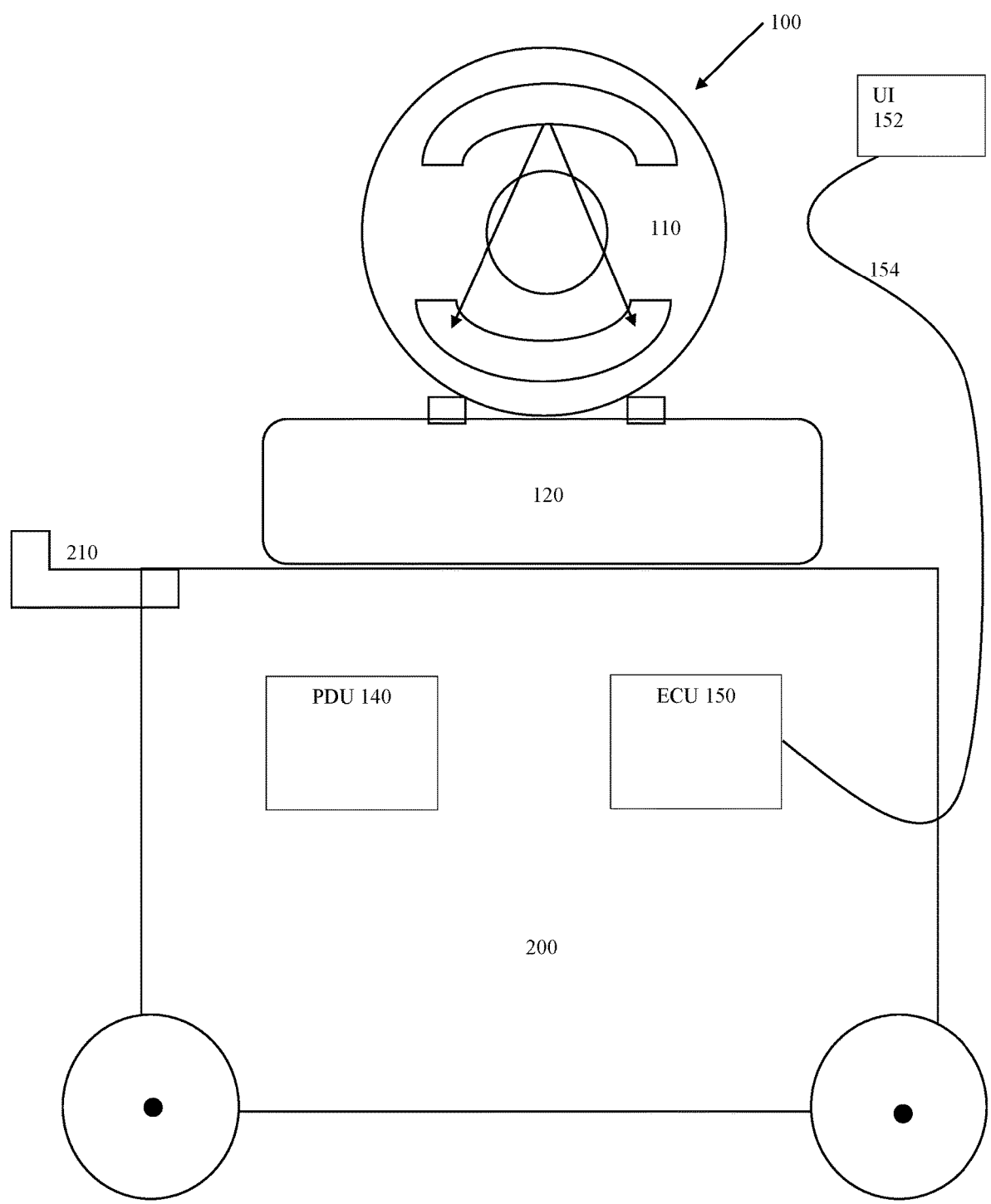
FIG. 2 depicts the exemplary CT system of FIG. 1 where the scanner component is mounted relative to a portable cart, according to embodiments of the present disclosure.

FIG. 2 depicts the exemplary CT system 100 of FIG. 1 where the scanner component 110 is mounted relative to a portable cart 200 with a drive bar 210. Notably, the cart 200 may be based on or adapted from an existing x-ray cart type assembly may be used to house the PDU 140 and ECU 150 assemblies. Alternatively, the control sub-system components and/or power sub-system components may be external to the CT system 100 and/or cart 200. In some embodiments, the mobile cart 100 may include a multi-directional drive system configured for independently controlling movement in multiple horizontal dimensions, e.g., forward/back and side-to-side. In some embodiments, the multi-directional drive system may be an omni-directional drive system such as a holonomic drive system which includes 3 degrees of freedom and is therefore able to shift from side-to side or strafe diagonally without changing the direction of its wheels. In some embodiments, omni-wheels or mecanum wheels or the like may be utilized to implement the omni-directional drive system. The use of omni-wheels or mecanum wheels may advantageously minimize surface drag and torque. Advantageously an H-drive drivetrain system may be utilized to supply power to each wheel station. Furthermore, as discussed above, the ECU assembly 150 may include a tethered/wired 154 user interface (UI) control assembly 152 for remote wired operation of the CT imaging system. The tether/wire 154 may advantageously provide a wired data connection while simultaneously protecting the UI control assembly 154 from loss or theft. In some embodiments, the tether/wire 154 may be retractable and the UI control assembly may be dockable with the CT system 100 and or with the cart 200. Advantageously the tether/wire may be long enough to enable remote control of the CT imaging system from a location that shields an operator from or otherwise mitigates the effects of radiation exposure. In some embodiments, a wireless data connection may be provided by the UI control assembly.

Figure 3:
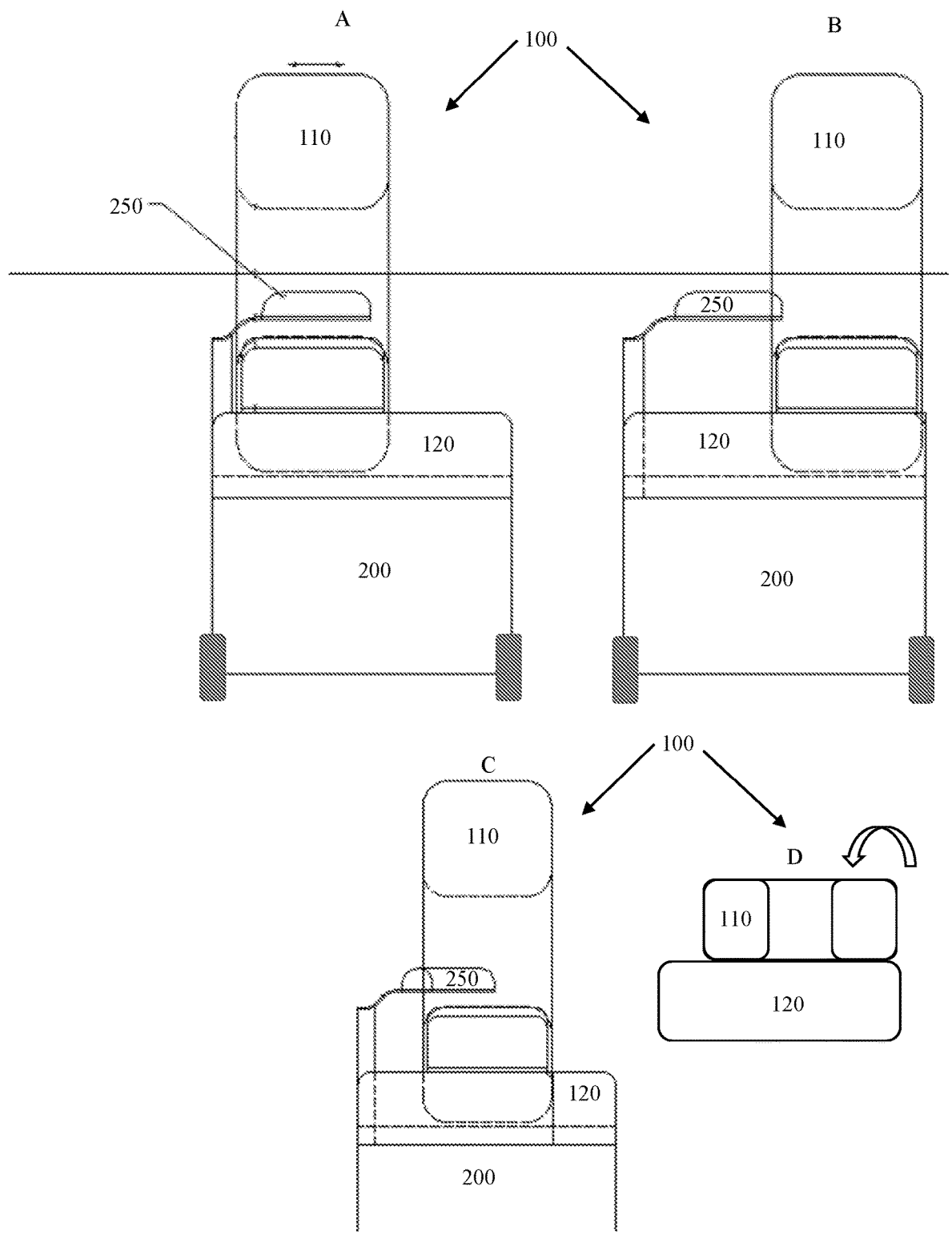
FIGS. 3A-3D illustrate an example real world application of the CT system if FIG. 2 including example scan positions and transport positions thereof, according to embodiments of the present disclosure.

FIGS. 3A-3D are used to illustrate an example real world application of the system 100 in FIG. 2. Notably, FIGS. 3A-3C illustrate the inclusion of an integrated patient alignment mechanism 250 (scan board) with respect to the exemplary CT system 100 of FIG. 2. The patient alignment mechanism 250 advantageously allows for proper alignment of a portion of the patient's anatomy relative to the CT system 100 without requiring special adapters for the ICU bed. A patient's bed (or other patient platform) is simply moved adjacent the alignment mechanism 250 and the height is adjusted to roughly correspond to the height of the alignment mechanism 250. The patient is then moved to place the desired portion of the patient's anatomy on the alignment mechanism. As noted above, proper alignment of the patient (e.g., of the portion of the patient's anatomy being scanned), is important achieving a proper scan and reducing image noise/artifacts. The alignment mechanism 250 may be secured relative to the base/platform 120 of the system. The use of an integrated patient alignment mechanism 250 that is secured relative to the CT system 100 as opposed to a patient platform ensures greater reliability and improves the ease of use of the CT system 100 by negating the need for different adapters depending for different types of patient platforms.

As described herein, in some embodiments, the integrated alignment mechanism 250 may include a latch or other releasable locking mechanism for securing the alignment mechanism relative to a patient platform. In some embodiments, a secure connection between the alignment mechanism and the patient platform may be required prior to initiating any scan. In further example embodiments, the integrated alignment mechanism may advantageously include one or more patient alignment features for guiding positioning of a patient, e.g., of a particular portion of a patient's anatomy, relative to the alignment mechanism. For example, the patient guide features may include markings, projections, grooves or other patient alignment features for positioning and orientating a patient relative to the alignment mechanism. The integrated alignment mechanism may further include one or more patient fasteners for securing a patient, e.g., a particular portion of a patient's anatomy in a particular position/orientation relative to the alignment mechanism. Thus, for example, in some embodiments, the integrated alignment mechanism may include one or more straps, ties, belts, clips or other patient fasteners.

Advantageously, the integrated patient alignment mechanism 250 may be configured for a particular portion of the patient's anatomy. For example, in some embodiments, the patient alignment mechanism 250 may include a headboard secured relative the system and adapted to facilitate proper alignment of a patient's head. In some embodiments, the patient alignment mechanism 250 may be interchangeable, e.g., in order to enable selection of the appropriate alignment mechanism for a particular portion of the patient's anatomy. In further example embodiments, the patient alignment mechanism 250 may define a plurality of different alignment configurations for the same portion of the patient's anatomy.

These different alignment configuration may, e.g., correspond to different scanning protocols/applications. In some embodiments, the patient alignment mechanism may enable controllably adjusting a position and/or orientation of a portion of the patient's anatomy, e.g., to a selected position/ orientation. Notably, the CT system 100 may be configured to register the selected configuration of the patient alignment mechanism with respect to the corresponding image data. In further example, embodiments, scanning protocols/applications may be pre-registered for a particular alignment mechanism and/or configuration thereof. Thus, in some embodiments, confirmation of a particular alignment mechanism and/or configuration thereof may be required by the system prior to initiating a corresponding scanning protocol/ application. In some embodiments, a scan sequence may be facilitated by automatically adjusting or otherwise guiding adjustment of patient orientation/alignment between scans. For example, in some embodiments, a scan sequence may involve automatically adjusting or otherwise prompting adjustment of a configuration of the alignment mechanism between scans. In other embodiments, a scan sequence may involve prompting swapping of a first alignment mechanism for a second alignment mechanism between scans.

FIGS. 3A and 3B depict an example patient example scan positions for the cart-based CT system 100. Advantageously, the scanning component 110 translates relative to the base 120 and the alignment mechanism 250 to perform a scan on a patient. Notably, the center of the x-ray beam is not limited to the depicted embodiments and may advantageously be more centered relative to a housing of the scanning component 110 (e.g. so as to provide for improved radiation shielding. Moreover, as described herein the housing of scanning component 110 may be extending or shaped to include additional radiation shielding that extends further down the patient. In example embodiments, the housing of scanning component 110 may include a nested (e.g., telescopic) housing including a first housing and a second housing. Moreover, in example embodiments, only a portion of the housing of the scanning component is configured to translate (e.g. a first housing component may translate over a second housing component). Alternatively, in some embodiments the housing may be configured to be stationary with the beam path itself translating internally within the housing (e.g., by translating an internal gantry rotationally associating a disk/drum with the housing). These and other embodiments are described in greater detail in other sections of the disclosure.

FIGS. 3B and 3D depict example transport positions for the for the cart-based CT system 100 of FIG. 2. In particular, in FIG. 3B the scanning component 110 may be advantageously advanced to a medial position so as to center weight distribution, e.g., with respect to the cart 200. Alternatively, in some embodiments, such as depicted in FIG. 3D the scanning component 110 may be configured to pivot, e.g., fold down relative to the base 120. This may allow for a lower distribution of gravity during transport and a more compact form factor, e.g., so as to facilitate storage of the CT system 100.

Figure 4:
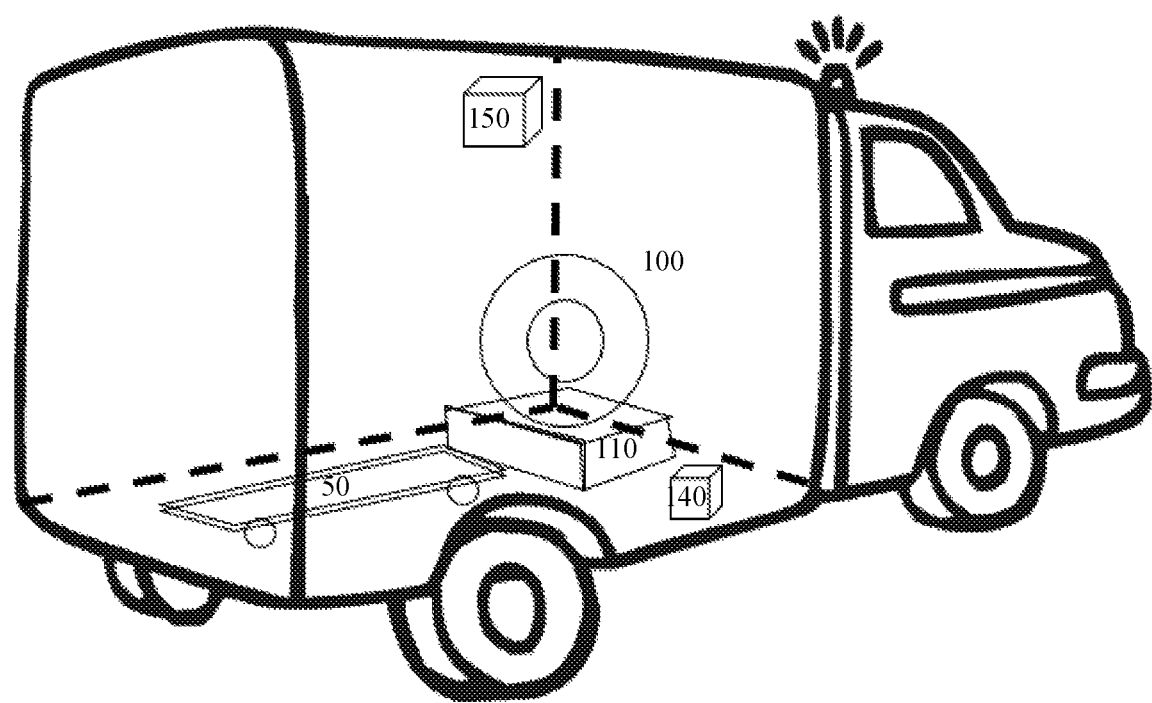
FIG. 4 depicts the exemplary CT system of FIG. 1 mounted relative to a first response vehicle, according to embodiments of the present disclosure.

FIG. 4 depicts the exemplary CT system 100 of FIG. 1 mounted relative to a first response vehicle. Note that the CT system 100 includes a low base/platform 110 configuration to align with a low stretcher 50 typically employed in the vehicle and to ensure a low center of gravity. In the depicted embodiment, the ECU 140 and PDU 150 assemblies are external to the CT system 100 and may be located anywhere in the vehicle.

Figure 5:
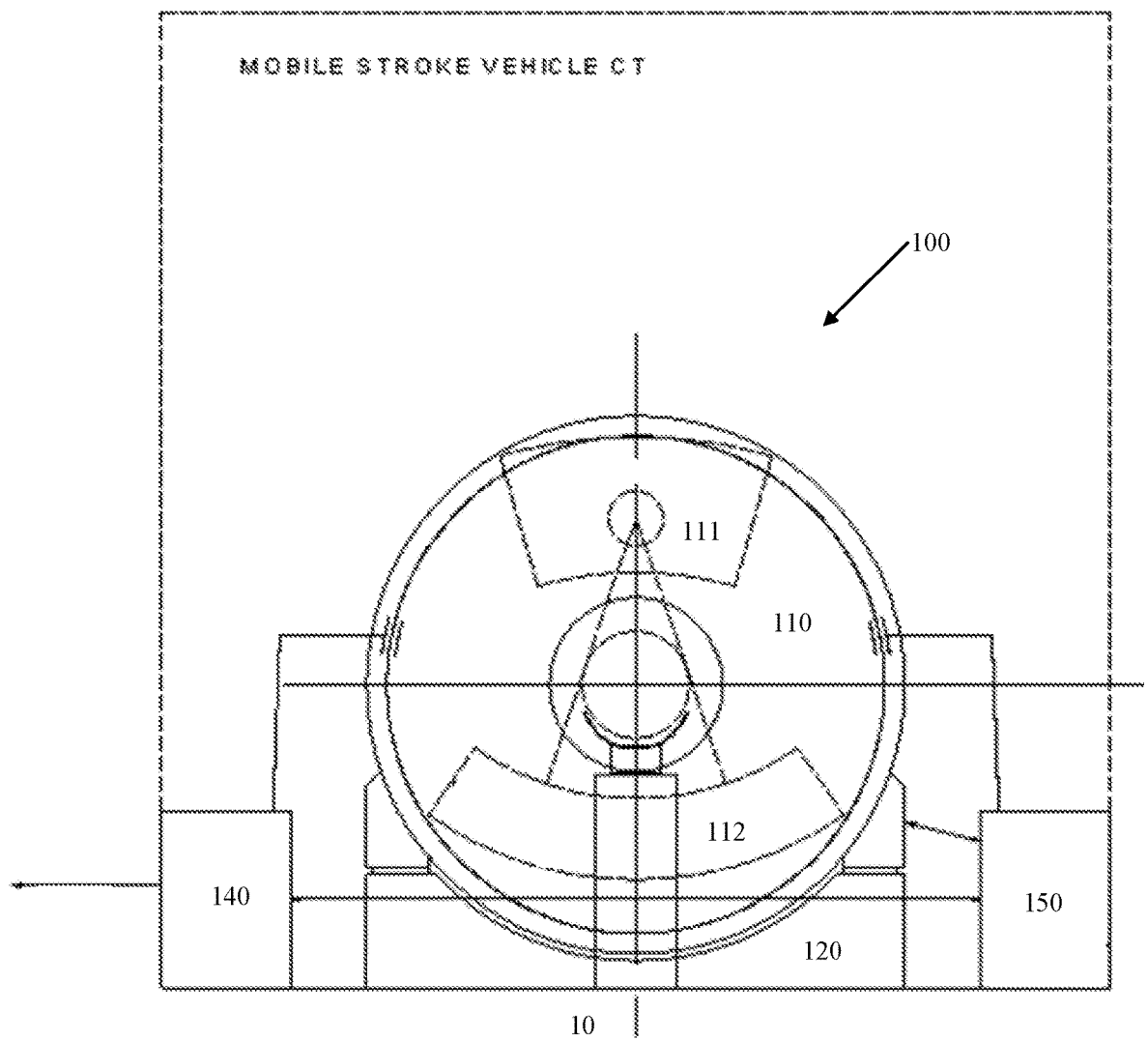
FIG. 5 depicts a more detailed schematic of the CT system for a first response vehicle depicted in FIG. 4, according to embodiments of the present disclosure.

FIG. 5 depicts a more detailed schematic of a CT system 100 for a first response vehicle, e.g., such as depicted in FIG. 4. As previously described with respect to FIG. 1, The CT system 100 includes a scanner component 110 in the form of a Ring/Doughnut assembly which includes two major assemblies: A) the x-ray generation box 111 which has x-ray tube, high voltage power supply (HVPS), collimator, etc. and B) the data acquisition system (DAS)/Detector/Control box 112 which contains all the detectors, spine, DAS, LVPS (low voltage power supply), interface electronics, data link electronics, etc. An internal drive system is also included for translating the scanner component 110 (e.g., in one or more axes) relative to a base/platform component 120. The system 100 further includes a power distribution unit (PDU) assembly 140 (that contains the power electronics and batteries) and Electronic Control Unit (ECU) assembly 150 (that contains the control, recon, and interface electronics). The ECU assembly 150 may further be operatively connected relative to a user interface (UI), and other control subsystems. As noted above, the ECU assembly 150 may include a tethered/wired user interface control assembly for remote wired operation of the CT imaging system. Furthermore the PDU assembly may advantageously be configured to require a minimal external power supply connection prior to allowing for operation of the CT imaging system. Thus, e.g., while the CT imaging system may include a battery back-up system for supplementing an irregular power supply, e.g., from a wall connection, a wired power supply connection may be required prior to operation of the device. Furthermore, as noted above, the ECU and PDU assemblies may be positioned anywhere within the first response vehicle.

Notably, the base/platform component 120 of the CT scanner 100 in FIG. 5 is securely mounted relative to a structural floor/frame 10 of the first response vehicle. This mounting of the CT scanner 100 relative to the floor of the first response vehicle provides a lower center of gravity for the CT scanner 100 as well as ensures a secure mounting during transport.

Figure 6:
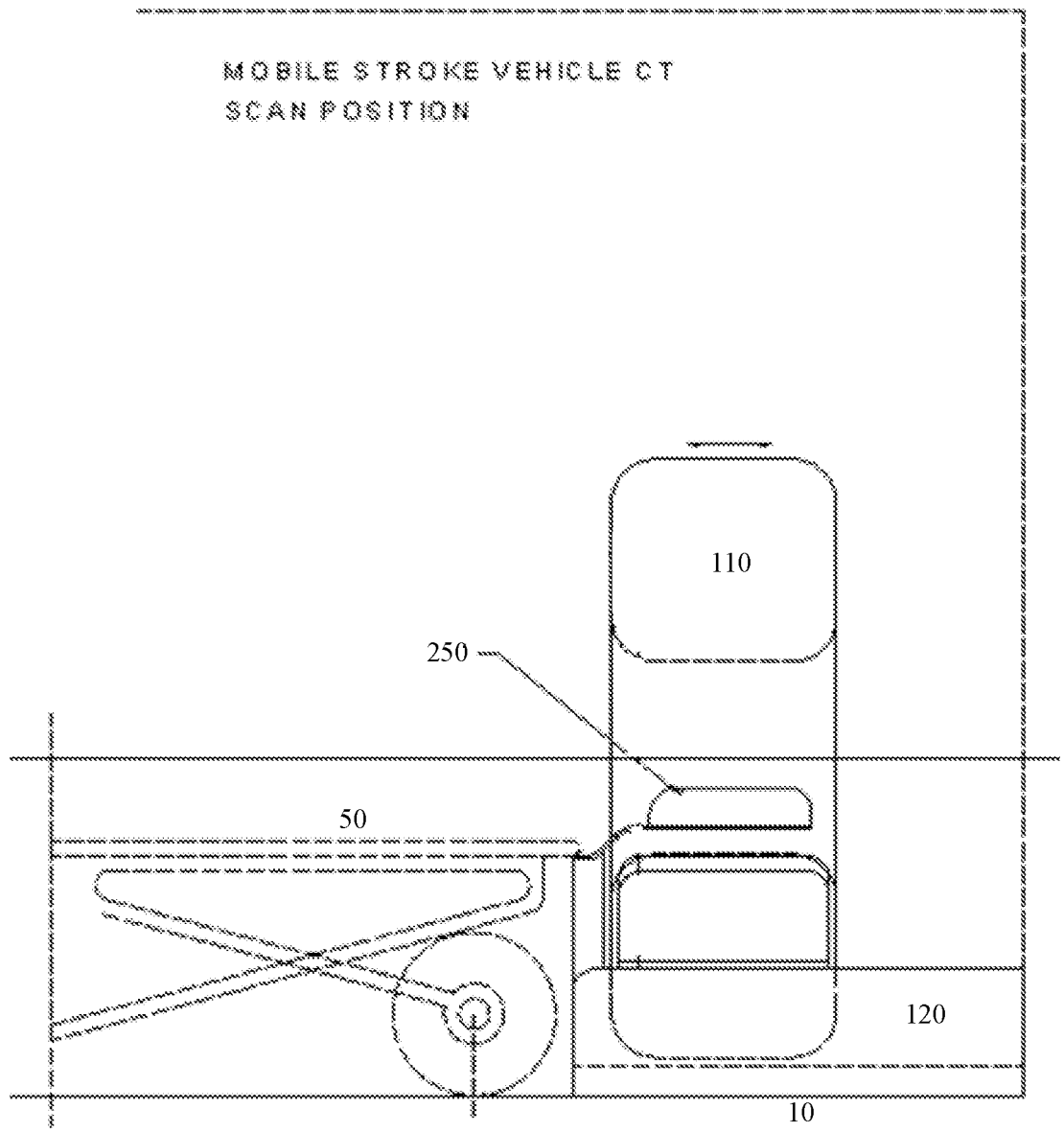
FIG. 6, illustrates the inclusion of an integrated patient alignment mechanism with respect to the exemplary CT system of FIG. 5, according to embodiments of the present disclosure.

FIG. 6 illustrates the inclusion of an integrated patient alignment mechanism 250 (scan board) with respect to the exemplary CT system 100 of FIG. 5. As noted above, the patient alignment mechanism 250 advantageously allows for proper alignment of a portion of the patient's anatomy relative to the CT system 100 without requiring special adapters for the ICU bed. In example embodiments, the patient alignment mechanism may act as an interface between a patient support structure and the CT system. For example, an ambulance or other mobile stretcher 50 may be positioned adjacent the alignment mechanism 250 and the height adjusted to roughly correspond to the height of the alignment mechanism 250. The patient then then moved to place the desired portion of the patient's anatomy on the alignment mechanism. As noted above, proper alignment of the patient (e.g., of the portion of the patient's anatomy being scanned), is important achieving a proper scan and reducing image noise/artifacts. As depicted, the alignment mechanism 250 is secured relative to the base/platform 120 of the system. As noted above, the use of an integrated patient alignment mechanism 250 that is secured relative to the CT system 100 as opposed to a patient platform ensures greater reliability and improves the ease of use of the CT system 100 by negating the need for different adapters depending for different types of patient platforms.

Figure 7:
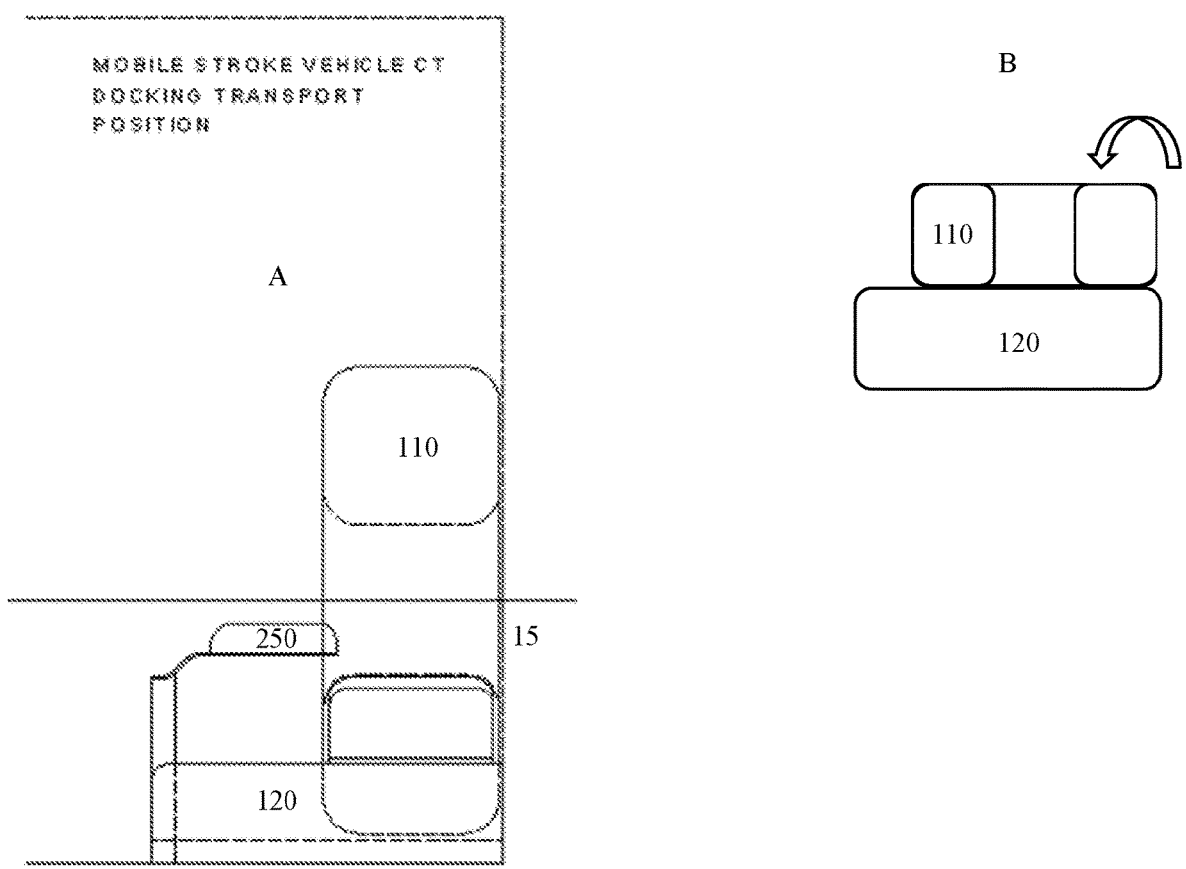
FIGS. 7A and 7B depict transport positions for the for the exemplary CT system of FIG. 5, according to embodiments of the present disclosure.

FIGS. 7A and 7B depict transport positions for the for the ambulatory CT system 100 of FIG. 5. In particular, in some embodiments, such as shown in FIG. 7A, the scanner component 110 may be translated so as to be placed adjacent a structural wall or support 15 in the first response vehicle. The scanner component 110 may then be secured relative to the wall/support 15 (e.g., using straps, belts, clips or other fasteners). Notably, in preferred embodiments, the wall/support may be a structural wall dividing the front (cockpit) of the ambulance from the back of the ambulance. Alternatively, in other embodiments, the wall/support may be a side wall or other structural feature such as a post or frame element. In some embodiments, such as depicted in FIG. 7B, the scanner component 110 may be configured to pivot, e.g., laterally (e.g., side-to-side) or between vertical and horizontal orientations. Such pivoting may advantageously facilitate positioning of the scanner component adjacent a support 15 for securing thereof. Alternatively, as depicted in FIG. 7B such pivoting may also further lower a center of gravity and provide better weight distribution during transport.

Figure 8:
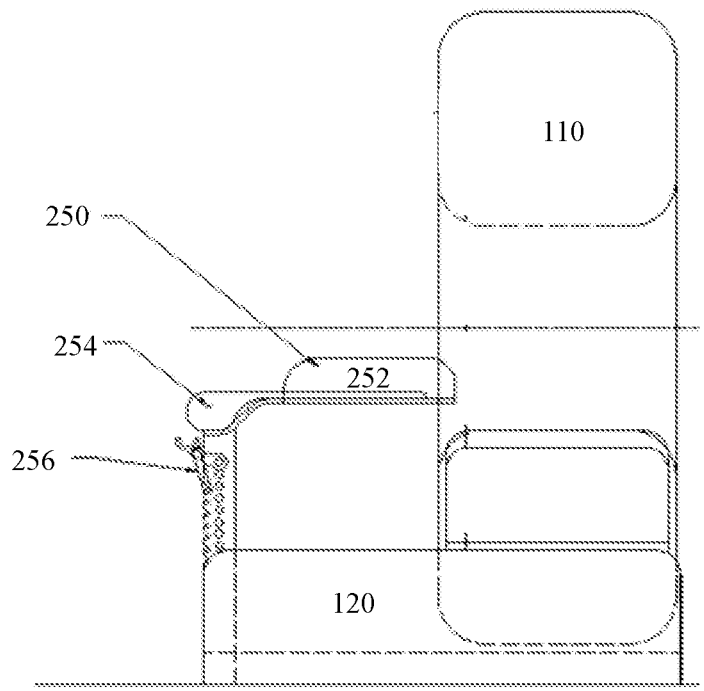
FIGS. 8 and 9 depict a more detailed schematic of an exemplary alignment mechanism which may be used in conjunction with the CT systems described herein, according to embodiments of the present disclosure.
Figure 9:
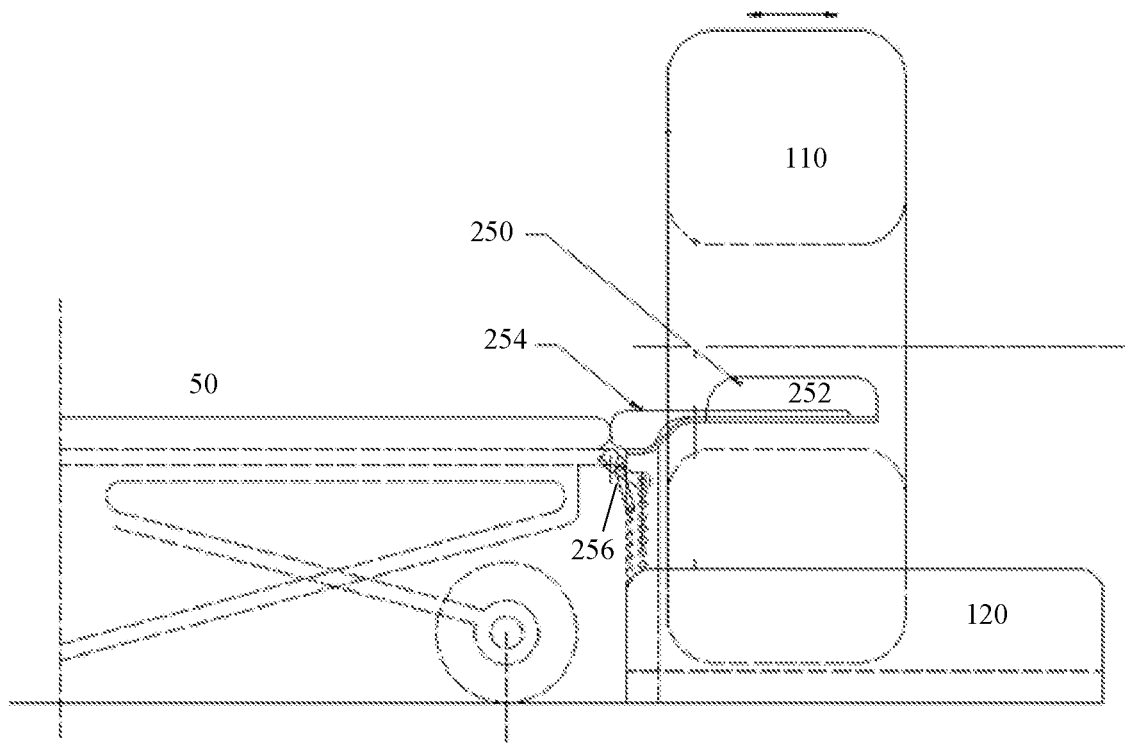

FIGS. 8 and 9 depict a more detailed schematic of an exemplary alignment mechanism 250 which may be used in conjunction with the CT systems described herein. In particular the example alignment mechanism 250 includes a head support 252 extending from a head support pad 254 which is attached via a post to the base/platform 120 of a CT scanner. The head support is configured to align with the center opening of the scanner component 110 of the CT scanner. Notably, the depicted alignment mechanism 250 also includes an adjustable latch type mechanism 256 for securing the alignment mechanism 250 relative to a patient platform such as bed 50. The latch may advantageously be height adjustable and configured to cooperate with a variety of different types of patient platforms.

Figure 10:
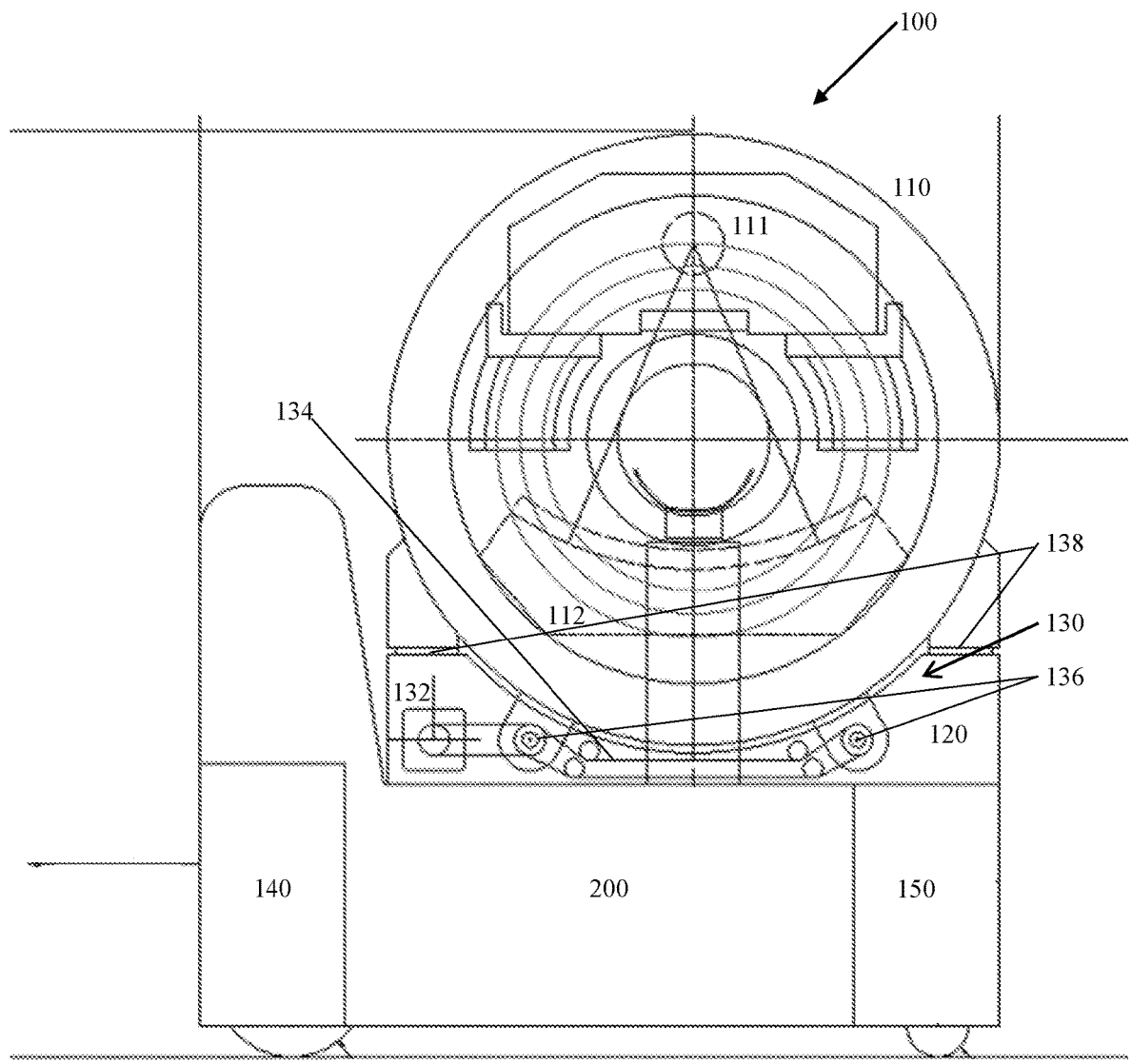
FIGS. 10 and 11 depict example drive configurations for example scanner components which may be used for the CT systems described herein, according to embodiments of the present disclosure.
Figure 11:
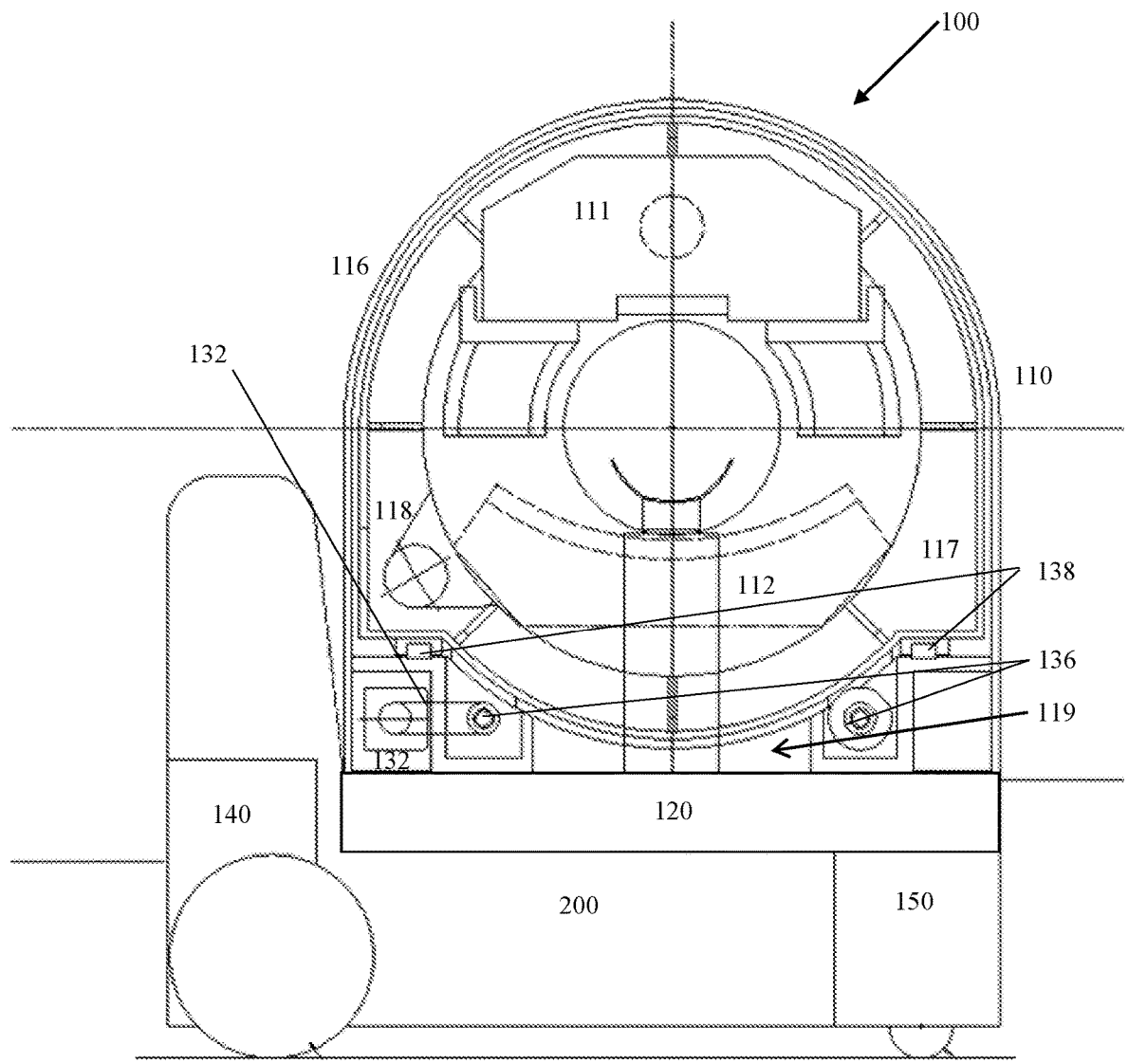
Figure 12:
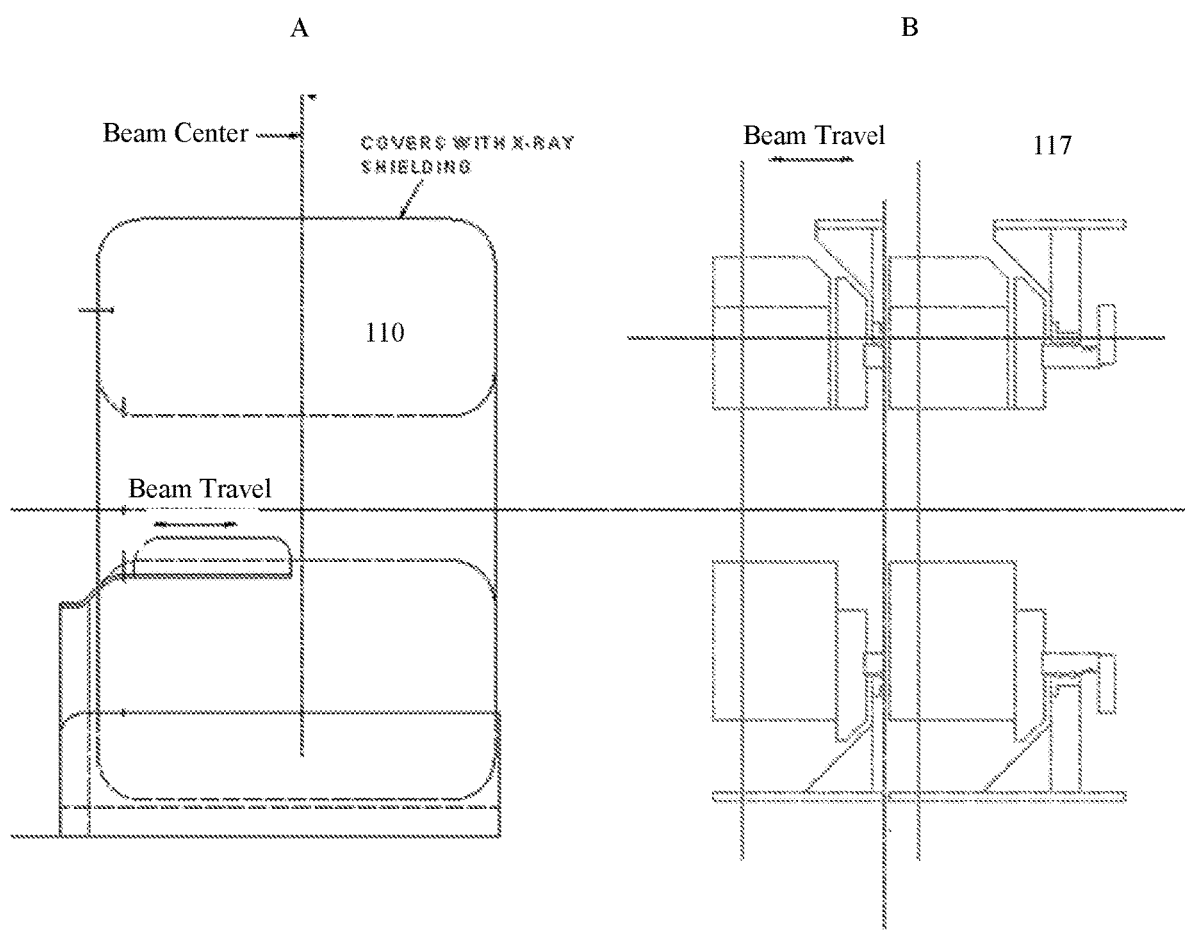
FIGS. 12A and 12B illustrate a translational mechanism for translating an internal gantry so as to allow for translation of the beam relative to a housing of the scanner component, according to embodiments of the present disclosure.

FIGS. 10 and 11 depict example configurations for CT systems 100 with different scan drive mechanisms. In particular, FIG. 10 depicts an example scan drive mechanism where the scanner component 110 is translated relative to base/platform 120 via an internal drive system 130. In particular a motor 132, drives belt 134, which in turn synchronously drives dual ball screws 136. Translational movement is aided by way of dual slides 138. FIG. 11 depicts an alternative drive mechanism where the scanner component 110 is stationary relative to base/platform 120. Thus, instead of the entire scanner component 110 translating relative to the base/platform 120, a rotational gantry 117 is translated relative to a stationary housing 116 of the scanner component 110 via a translational drive system 119. This is shown in greater detail in FIGS. 12A and 12B. In particular, the translation of the gantry 117 from a first position to a second position is depicted in FIG. 12B with the corresponding beam path travel relative to the housing depicted with respect to FIG. 12A. In example embodiments, the translational drive system 119 of FIG. 11 may be similar to the internal drive system 130 of the embodiments of FIGS. 1 and 10 and include a motor 132 to drive ball screws 136 via belt 134 which actuate translational movement of the gantry 117 as defined by slide mechanism 138. One advantage of the embodiment of FIG. 11 over the embodiment of FIG. 10 is that all translational scanning motion is contained within an enclosed housing 116 and therefore is not perceptible by the patient. Advantageously, this can reduce collision risks with the patient. In some embodiments, scan drive mechanisms of FIGS. 10 and 11 can be combined in a single embodiment, e.g., where the housing is able to translate relative to the patient independent of the gantry translating within the housing. Notably, the drive systems depicted in FIGS. 10 and 11 may advantageously utilize a V-belt type of drive system to rotate an internal disk/drum assembly.

Figure 13:
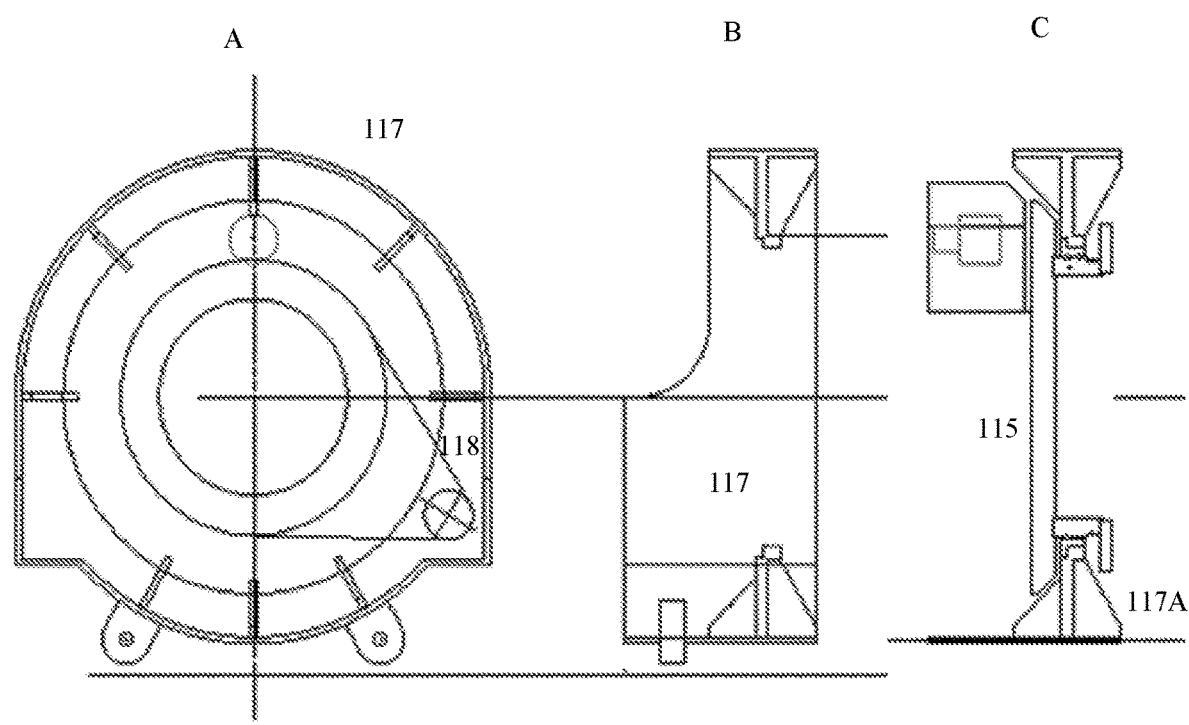
FIGS. 13A-13C depict a more detailed schematic of a drive system from an example scanner component including a rotational gantry, according to embodiments of the present disclosure.

FIGS. 13A-13C depict a more detailed schematic of internal components of an exemplary rotational gantry 117. In particular, a rotating disk or drum assembly 115 may be rotationally mounted relative to the gantry 117. Note that the gantry may advantageously include one or more bearing runs 117. In particular, the gantry 117 may include an annular outer support having a radially inwardly facing, continuous circumferential bearing chamber including two circumferential bearing runs within the bearing chamber where roller bearings in the bearing runs rotatable support a circumferential lip of the drum or disk within the outer support, such that the drum or disk is rotatable about an axis of rotation. A rotational drive system 118, such as a belt or gear drive system may be utilized to drive rotation of the drum or disk 115 within the gantry 117. For example a poly-v belt drive system or other belt drive system may be utilized to transfer rotation from a drive pulley, e.g., a sheaved drive pulley, to the drum or disk. Notably, the rotational mounting and drive components of the systems described herein are not limited to particular examples provided above. Advantageously, in some embodiments (such as depicted in FIG. 10) the gantry 117 may include/form an external housing for the scanning component 110.

Figure 14:
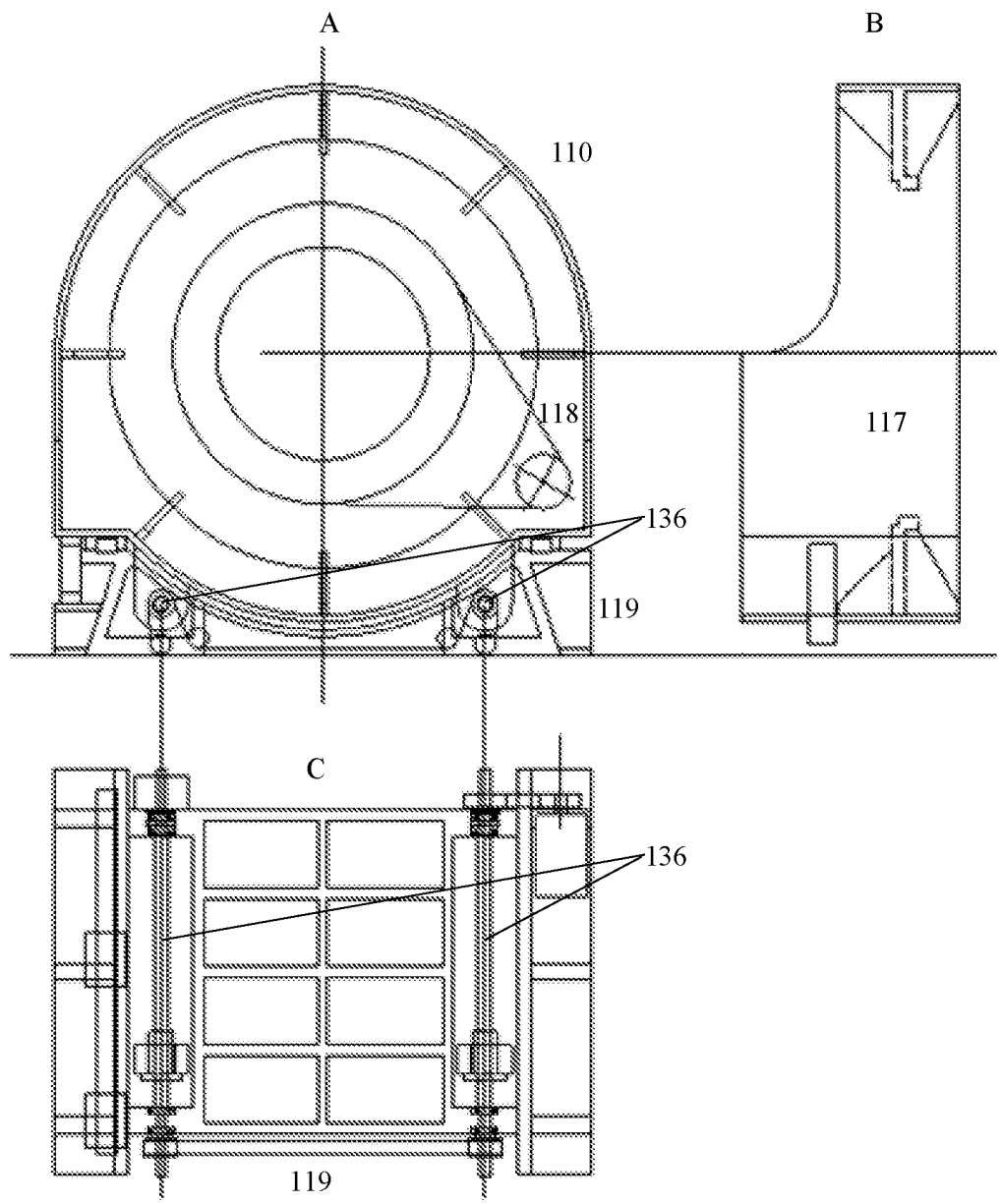
FIGS. 14A-14C depict a variation of the drive system of FIGS. 13A-13C where the rotational gantry 117 is translatably mounted relative to the housing 116 of the scanner component, according to embodiments of the present disclosure.

In other embodiments, the gantry 117 may be translatably mounted within an external housing of the scanning component 110, e.g., via an internal translational drive system 119 (see, e.g., FIG. 11). FIGS. 14A-14C depict a more detailed view of the rotational gantry 117 and internal translational drive system 119, of FIG. 11. In particular, the translational drive system 119 includes dual ball screws 136 where rotation of the screws results in translational movement of the gantry 117 relative to the housing (see, e.g., FIG. 11). The result is a scanning component 110 with a variable beam path position. Thus, rather than translate the scanning component 110, the scanning component 110 may remain stationary while the beam bath is shifted internally by translation of the of the rotation drum/disk via translation of the gantry 117.

Figure 15:
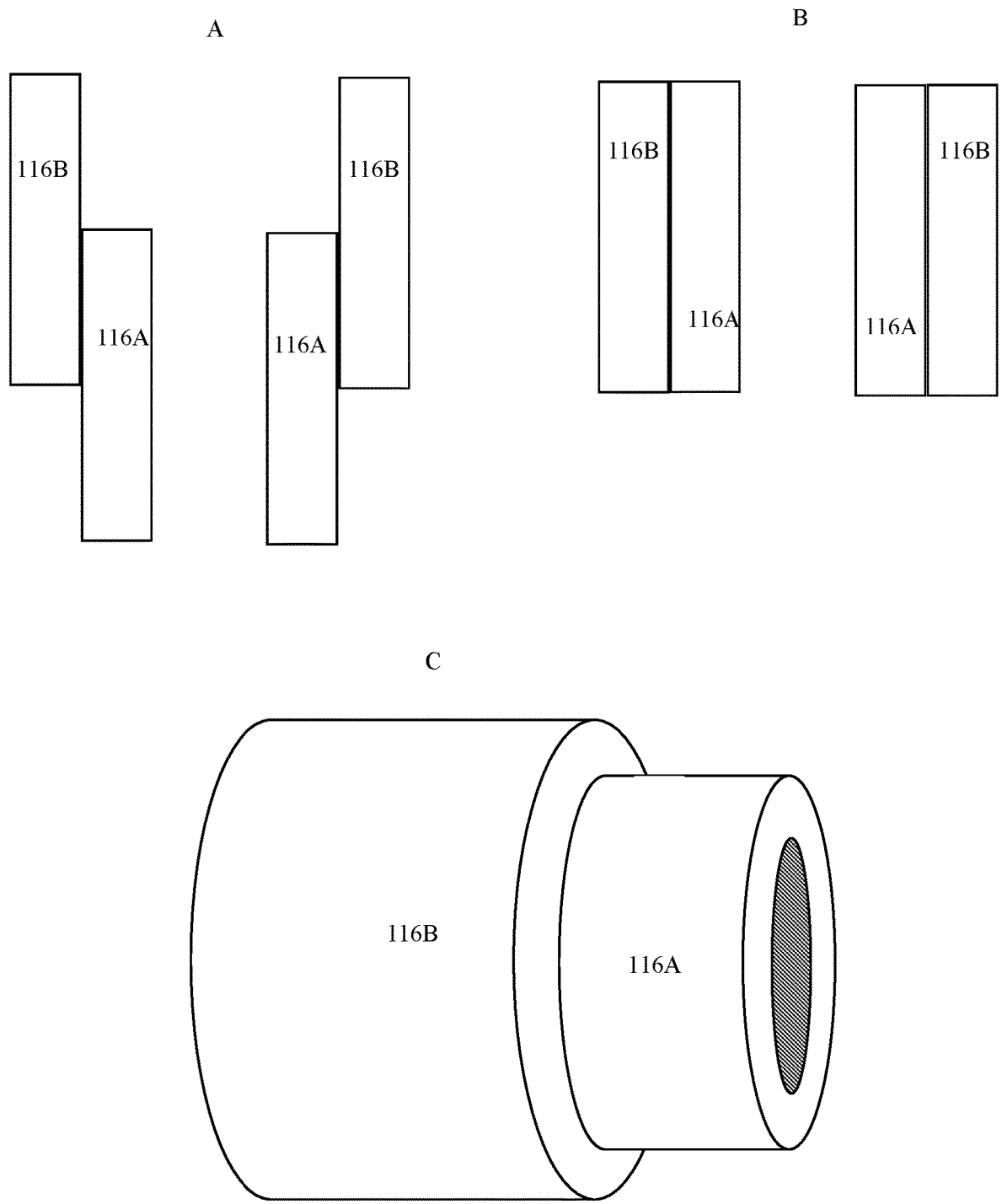
FIGS. 15A-15C, 16A, 16B, 17A and 17B illustrate how, in example embodiments, the CT systems presented herein may include a nested scanner component configuration, according to embodiments of the present disclosure.

FIGS. 15A-15C, 16A, 16B, 17A and 17B illustrate how, in example embodiments, the CT systems presented herein may include a nested, e.g., a telescopic scanner component configuration. In a nested configuration a first housing 116A of the CT scanner component (which may in some embodiments be an outer housing) may be advantageously nested within a second housing 116A of the CT scanner component (which in some embodiments may be an inner housing). In some embodiments, the first and second housings 116A and 116B may have the same length. In other embodiments, the first and second housings 116A and 116B may have different lengths, e.g., housing 116A may have a shorter length than the second housing 116B. As depicted, the first and second housings 116A and 116B may each include a ring-shaped housing member. More particularly, the first and second housings 116A and 116B may be generally shaped as nested right circular hollow cylinders (although the shape may be slightly modified to allow for a drive system for a rotational gantry (positioned with within one or more of the housings) such as depicted in other embodiments described herein). In example embodiments, such as depicted in FIGS. 15A-15C, the first and second housings 116A and 116B may be nested with the first housing 116A positioned within a central opening defined by an inner diameter of the second housing 116B. This nesting configuration is similar to a Russian nesting doll configuration. Thus, in some embodiments, the first housing 116B may include an inner diameter substantially equal to an outer diameter of the second housing 116A. Alternatively, as is further described in other embodiments depicted herein such as in FIGS. 16A, 16B 17A and 17B, the second housing 116B may define a nesting slot (e.g., between outer and inner diameters thereof) for receiving the first housing 116A therein.

Generally, the first and second housings 116A and 116B may independently or cooperatively define one or more enclosed cavity spaces for receiving and housing parts of CT scanner component. For example, as is further described in the embodiments of FIGS. 16A, 16B 17A and 17B, in some embodiments, first and second housings 116A and 116B may cooperate to define an inner cavity space for housing internal parts of the CT scanner component such as a disk or drum assembly (with x-ray generation and detection sub-assemblies), a rotational gantry for the drum or disk assembly, a rotational drive system for the disk or drum assembly and (optionally) a translational drive system for the rotational gantry (which may advantageously allow for translation of the rotational gantry within the enclosed cavity space such as specifically depicted in the embodiment of FIGS. 16A and 16B). In other embodiments, the first and/or second housings may each individually define an enclosed cavity space. Thus, for example, the first housing 116A may independently define an enclosed cavity space for receiving the internal parts of the CT scanner component.

Figure 16:
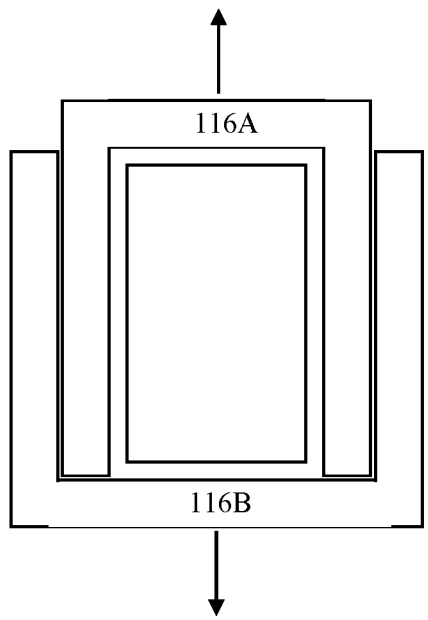
Figure 16:
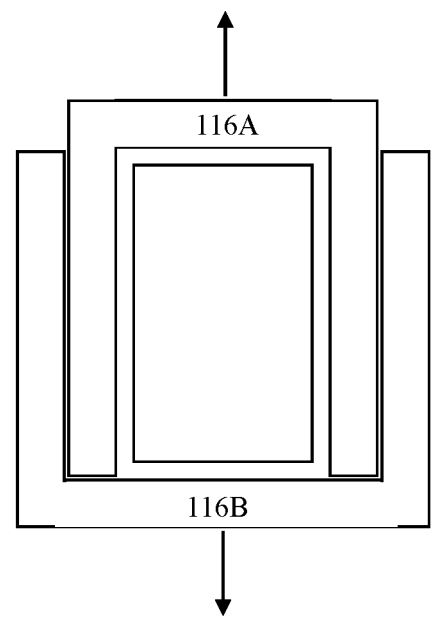
Figure 16:
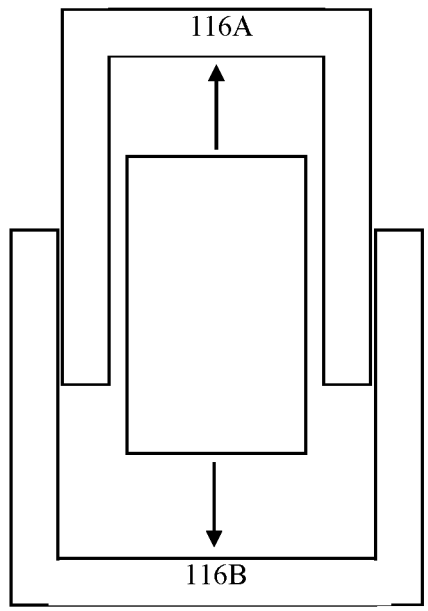
Figure 16:
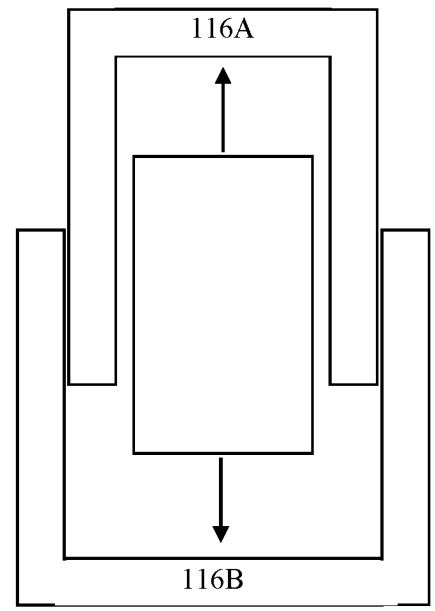
Figure 17:
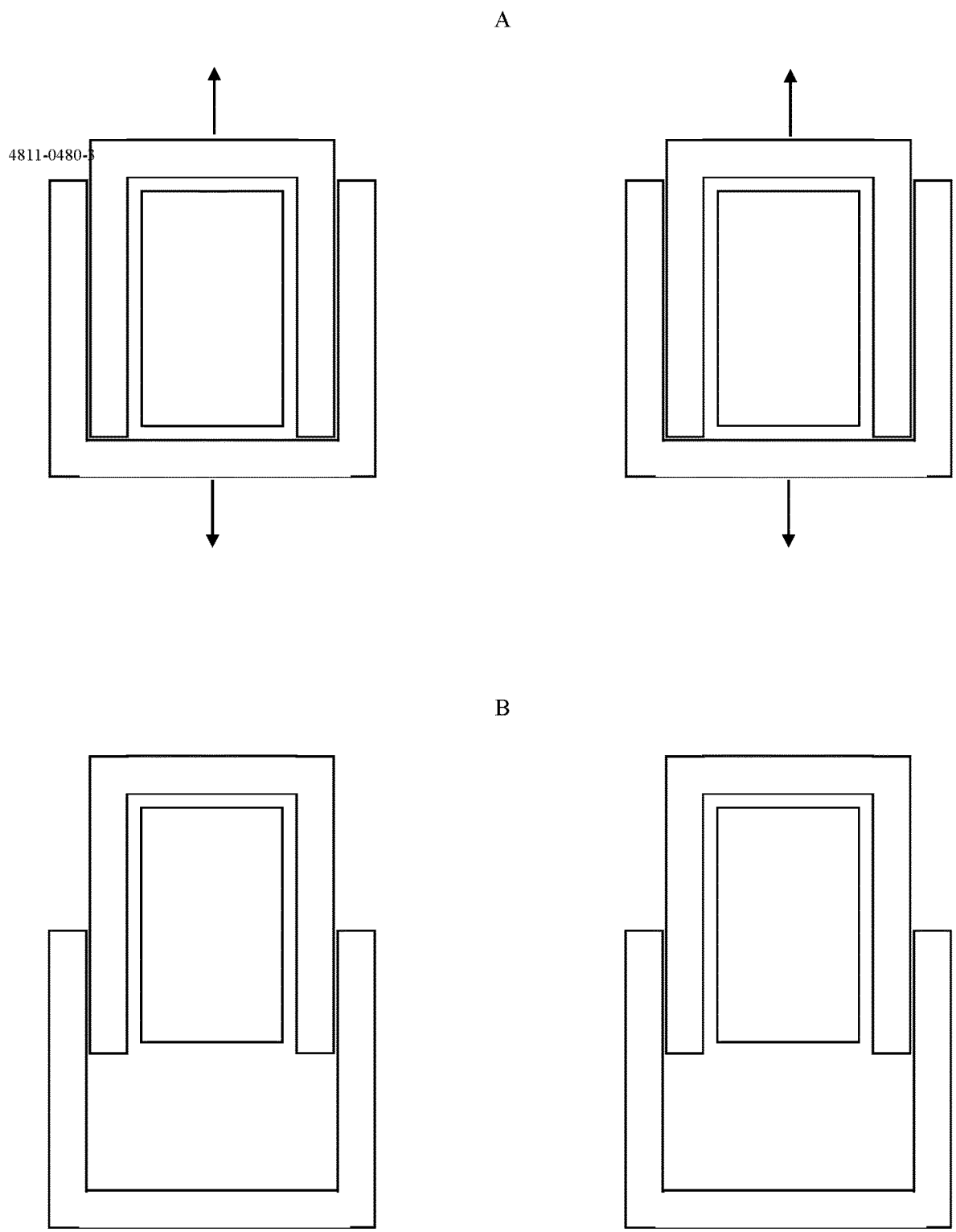

FIGS. 16A and 16B depict one example embodiment of a nested configuration, where first and second housings 116A and 116B may cooperate to define an inner cavity space for housing internal parts of the CT scanner component. Notably, in the embodiment of FIGS. 16A and 16B the CT scanner component may include a translational drive system for internal translation of a rotational gantry within the inner cavity space defined by the first and second housings 116A and 116B. FIGS. 17A and 17B depict an alternative embodiment to that in FIGS. 16A and 16B that does not include a translational drive for the rotational gantry. Thus, in the embodiment of FIGS. 17A and 17B, the internal parts of the CT scanner component are fixed relative to one of the housings (e.g., relative to the first housing 116A).

As was previously described herein, there are a number of different ways a scan may be conducted using the systems and methods described herein. For example, in some embodiments, such as depicted in FIGS. 16A and 16B, a translational drive system for a rotational gantry may allow for internal translation of the rotational gantry within an enclosed cavity space defined by one or more housings. This method of scanning advantageously, enables maintaining a stationary housing relative to the patient during scanning. In other embodiments, such as depicted in FIGS. 17A and 17B, the rotational gantry may move in conjunction with one or more housings (for example, the rotational gantry may be secured relative to a first housing 116A which translates relative to a second housing 116B). It is noted, that in some embodiments, a scan may combine internal and external scanning techniques (e.g., a rotational gantry may move within a housing and the housing itself may also move).

Note that there are many advantages to a nested housing structure including from a collapsibility standpoint as well as for added radiation protection and better scanning functionality. In some embodiments, such as depicted in FIGS. 15A-C a first housing 116A may define an inner opening configured. e.g., sized/shaped, for receiving a first portion of a patient's anatomy (such as the patient's head) while a second housing 116B defines a wider opening configured for receiving a greater portion of a patient's anatomy (such as a patients head neck and shoulders). Thus, in some embodiments, the second housing 116B may advantageously act as a radiation shield, e.g., to help contain radiation from the scanner component and mitigate radiation scatter.

In some embodiments, the first housing 116A may be stationary or fixed relative to the second housing 116B. Thus, in some embodiments, the first housing component 116A may include an internal translation drive for translating a rotatable disk/drum housed therein (e.g., thereby translating a beam bath relative to a patient). In other embodiments, the first housing may 116A be configured to translate relative to the second housing 116B. FIGS. 15A versus 15B, 16A versus 16B and 17A versus 17B illustrate examples of such translational movement. In some embodiments, this may be for storage/alignment purposes, e.g., for enabling collapsing the first housing into the second housing (such as depicted in FIGS. 15B, 16A and 17A) so as to reduce a size footprint of the CT scanner component when the scanner component isn't in use, to enable positioning of the scanner relative a portion of a patient's anatomy to be scanned and/or to enable positioning one or more housings in a position to provide optimal radiation shielding for a particular scan position. In some embodiments, the first housing 116A may be configured to telescopically extend relative to the second housing 116B (see, e.g., FIGS. 15A, 15C, 16B and 17B), e.g., prior to initiating a scan. Advantageously, in some embodiments, this may provide for enhanced radiation shielding (see, e.g., FIGS. 15A and 15C). In other embodiments, this may elongate/define an internal cavity for internal translation of scanning components (see, e.g., FIG. 16B). In further embodiments, the first housing 116A may be configured to translate relative to the second housing 116B so as to implement a scan, e.g., so as to translate a beam path relative to the patient (see, e.g., FIG. 17B). Thus, in some embodiments, the first and/or second housing(s) may be positioned relative to the patient so as to align the CT scanner component with the patient. The first and or second housing(s) may further be positioned relative to the patient or one another so as to provide optimal radiation coverage. A scan may then be initiated, e.g., by either by translating the first housing 116A relative to the second housing 116B (e.g., so as to translate a beam path relative to the patient) or by translating scan components internally (e.g., within a cavity space defined by the first and/or second housing(s)). Notably, in some embodiments, to provide optimal radiation shielding the CT scanner component may be configured such that the beam path is maintained in a central positioning relative to the first and/or housings. This may advantageously minimize radiation scatter and unwanted exposure by the patient and/or a care provider.

In some embodiments, the first and second housings 116A and 116B may be configured to be partially nested and may cooperate to define a contiguous outer surface. Thus, in example embodiments, the contiguous outer surface may include a variable outer diameter (e.g., with the first housing 116A including a smaller outer diameter than the outer diameter of the second housing 116B such as to enable the first housing 116A to fit within the second housing 116B). In other embodiments, the contiguous outer surface may be fully defined by the second housing 116B with the first housing 116A being fully nested within the second housing 116B. As noted above, in some embodiments, the first and second housings 116A and 116B may be fixed relative to one another. Thus, in some embodiments, the first housing 116A may be fixed in a fully nested position within the second housing 116B, e.g., wherein the first housing is shorter in length than the second housing and the first housing is positioned off-center (e.g.,) adjacent one of the openings of the second housing. In some embodiments, the first and second housings may be constructed as a unitary housing.

In example embodiments, a telescoping housing may be utilized as follows: A patient can be placed on a headboard, which is solidly attached and aligned with a fixed base. A front housing may then translate over the patient's head (either manually or by motorized mechanism). Once the patient's head is safely inside the scan bore, an inner translating CT mechanism (enclosed translating gantry) can then translate forward all the way to the front housing getting the x-ray beam deep down towards the patient's neck. Scanning can take place whereby the scanner translates while it scans (either spiral, or step and shoot) towards a top of patient's head. When the scan is complete, the internal translating gantry may then translates all the way to a back housing, and the front housing may then be collapse into the front housing and locked into place. The translate motor system for the CT is generally low torque with a safety stall feature so it never has the "crushing" force to hurt/injure the patient in any way. Advantageously, for the example scan method described above, systems and methods disclosed herein can utilize higher torque during scanning (since the patient is isolated from the motion of the scanner). Therefore if mounted in a vehicle it can be operated on an incline and not have to worry about having to torque to overcome gravity. This is a weakness in previous vehicle mounted CT systems, they have to be operated on a level surface or the vehicle must contain leveling mechanisms. As noted herein, the housing/covers may be constructed of material to shield radiation. The deep bore that is created by expanding the housing is present during the scan is able to contain a large amount of the scattered radiation thus resulting in much less exposure to hospital personnel. The headboard being pre-aligned in a solid fashion to the base of the scanner makes sure that all scans are done perfectly straight. It also creates a condition whereby the patient's head is centered in the opening and is not in jeopardy of collision with the covers when they are put over the patient.

Advantageously, the scanner systems as described herein may be mounted relative to a motorized drive system like the portable x-ray systems of the hospital making it easy to move around from room to room. This mechanism can be made very sturdy and rugged as opposed to needing very precise motion. It can therefore overcome obstacles such as door thresholds, elevators, debris on floor, etc. It is advantageous for this drive system to be separate from the scan drive system.

Advantageously, the scanner systems disclosed herein may include battery power for maintenance of operation when disconnected from the wall for charging. Thus x-ray power can also be greater than the power available wall power.

The user interface for CT scanners has normally been a complex computer based system with keyboard/mouse. The systems disclosed herein advantageously may utilize a very simple tablet-like interface that is connected via cable/dongle to the scanner. The cable/dongle is of sufficient length to allow the operator to move safely outside the radiation zone of the scanner yet still be within visual distance of scanner to provide emergency stop of the mechanism should a hazard arise. The cable/dongle also deters theft of the tablet. The Tablet UI system can then communicate with the hospital/radiology information systems to communicate patient information and data.

The scanner systems provided herein may include translation with sub-millimeter precision to provide accurate tomographic slice images of the patient's anatomy. As described above, this precision may be accomplished by having one or two precision ball screws connected to the base and the bottom of the scanner. The scanner may further be mounted on one or two low friction linear slides. By turning the ball screw the gantry will move precisely in translation. If two ball screws are used, they can be synchronized by belt and pulley, or by gear mechanism. The ball screw can be rotated by connection to a precision electric motor and motion drive system. It can be of servo or stepper motor type. The motor can be a direct mount to the ball screw. It is preferred to mount the motor to the ball screw with belt and pulley(s). Optionally the motor can be linked to the ball screw by gear(s). Gears or pulley(s) can be sized to provide more or less mechanical advantage and precision.

Additional advantageous features of example embodiments described herein are adaptable across different application. Thus, in some embodiments a cart-based (ICU) and vehicle based (Mobile Stroke CT) system can share a same scanner component and base. More particularly, a base of a scanner component can be interchangeable mounted to either to a transport cart or to a floor/frame of a first response vehicles.

Whereas many alterations and modifications of the disclosure will no doubt become apparent to a person of ordinary skill in the art after having read the foregoing description, it is to be understood that the particular embodiments shown and described by way of illustration are in no way intended to be considered limiting. Further, the subject matter has been described with reference to particular embodiments, but variations within the spirit and scope of the disclosure will occur to those skilled in the art. It is noted that the foregoing examples have been provided merely for the purpose of explanation and are in no way to be construed as limiting of the present disclosure.

While the present inventive concept has been particularly shown and described with reference to exemplary embodiments thereof, it will be understood by those of ordinary skill in the art that various changes in form and details may be made therein without departing from the spirit and scope of the present inventive concept as defined by the following claims.

The invention claimed is:

1. A CT system comprising:
   a scanner component;
   a base component mounted relative to a mobile cart wherein the mobile cart includes a motorized transport drive system and more than one wheel element that supports the mobile cart and
   wherein the mobile cart transports the scanner and base components in a first direction; and
   an internal drive component for translating the scanner component relative to the base component in a second direction transverse to the first direction;
   wherein the scanner component is located between at least one pair of wheel elements in both the first and second directions.

2. The CT system of claim 1, wherein the system further includes a patient alignment mechanism mounted directly to the CT system.

3. The CT system of claim 2, wherein the patient alignment mechanism is a headboard.

4. The CT system of claim 2, wherein the patient alignment mechanism is mounted relative to the base component.

5. The CT system of claim 1, wherein the CT system includes a plurality of modular subsystems.

6. The CT system of claim 5, wherein the plurality of modular sub-systems include an x-ray source sub-system, a detection sub-system, a control sub-system and a power sub-system.

7. The CT system of claim 1, wherein the mobile cart includes an omni-directional drive system for transporting the mobile cart.

8. A CT system comprising:
a scanner component;
a base component configured for mounting to a mobile cart, wherein the mobile cart transports the scanner and base components in a first direction and wherein the mobile cart includes more than one wheel element that supports the mobile cart; and
an internal drive component for translating the scanner component relative to the base component in a second direction transverse to the first direction,
wherein the scanner component is located between at least one pair of wheel elements in both the first and second directions,
wherein the base component is also configured for interchangeable mounting to a vehicle floor.

\* \* \* \* \*